United States Patent
Bergstein

(10) Patent No.: US 12,357,700 B2
(45) Date of Patent: Jul. 15, 2025

(54) COMBINATION THERAPY METHOD OF TREATING MYELOPROLIFERATIVE NEOPLASMS WITH A DIPHTHERIA TOXIN-HUMAN INTERLEUKIN-3 CONJUGATE IN COMBINATION WITH OTHER AGENTS

(71) Applicant: Stemline Therapeutics, Inc., New York, NY (US)

(72) Inventor: Ivan Bergstein, New York, NY (US)

(73) Assignee: Stemline Therapeutics, Inc., New York, NY (US)

( * ) Notice: Subject to any disclaimer, the term of this patent is extended or adjusted under 35 U.S.C. 154(b) by 843 days.

(21) Appl. No.: 17/289,898

(22) PCT Filed: Oct. 30, 2019

(86) PCT No.: PCT/US2019/058769
§ 371 (c)(1),
(2) Date: Apr. 29, 2021

(87) PCT Pub. No.: WO2020/092505
PCT Pub. Date: May 7, 2020

(65) Prior Publication Data
US 2022/0001020 A1 Jan. 6, 2022

Related U.S. Application Data

(60) Provisional application No. 62/832,558, filed on Apr. 11, 2019, provisional application No. 62/753,145, filed on Oct. 31, 2018.

(51) Int. Cl.
| | | |
|---|---|---|
| A61K 47/64 | (2017.01) | |
| A61K 31/519 | (2006.01) | |
| A61K 31/706 | (2006.01) | |
| A61K 38/20 | (2006.01) | |
| A61K 38/45 | (2006.01) | |
| A61P 35/00 | (2006.01) | |

(52) U.S. Cl.
CPC .......... *A61K 47/642* (2017.08); *A61K 31/519* (2013.01); *A61K 31/706* (2013.01); *A61K 38/202* (2013.01); *A61K 38/45* (2013.01); *A61P 35/00* (2018.01)

(58) Field of Classification Search
CPC .. A61K 47/642; A61K 38/202; A61K 38/164; A61P 35/00
See application file for complete search history.

(56) References Cited

U.S. PATENT DOCUMENTS

2018/0071296 A1  3/2018  Cao et al.
2018/0071302 A1  3/2018  Abella et al.

FOREIGN PATENT DOCUMENTS

WO    2008030539 A2    3/2008

OTHER PUBLICATIONS

Hasselbalch H.C. et al., "Perspectives on interferon-alpha in the treatment of polycythemia vera and related myeloproliferative neoplasms: minimal residual disease and cure?" Seminares in Immunopathology, 2019, vol. 41, pp. 5-19 (15 pages), published online Sep. 10, 2018.
Melikyan A.L. et al., "Cepeginterferon Alpha-2b in the treatment of chronic myeloproliferative diseases," Therapeutic Archive, 2018, No. 7, pp. 23-29 (7 pages).
Anonymous: "SL-401 in Combination With Azacitidine or Azacitidine/Venetoclax in Acute Myeloid Leukemia (AML) or High-Risk Myelodysplastic Syndrome (MDS)" URL:https://clinicaltrials.gov/ct2/show/re cord/NCT03113643?term=SL-401&draw=2&rank=2 [retrieved on Jan. 31, 2020]; pp. 1-10, (2017).
Hunter et al., "Current Management and Recent Advances in the Treatment of Chronic Myelomonocytic Leukemia", Current Treatment Options in Oncology, (19(12), pp. 1-14 (2018).
International Search Report issued in International Application No. PCT/US2019/058769, dated Feb. 10, 2020; 15 pages.
Patnaik, M. "Resutls from Ongoing Phase 1/2 Trial of SL-401 in Patients with Myeloproliferative Neoplasms Including Chronic Myelomonocytic Leukemia and Primary Myelofibrosis", 59th ASH Annual Meeting (103)(suppl. 1), pp. 1-7, (2017).
Pettit et al., "Novel Therapies for Myelofibrosis", Current Hematologic Malignancy Reports, Current Science Inc., Philadelphia, PA, US (12)(6), pp. 611-624 (2017).
Stephansky, J. "Resistance to SL-401 in AML and BPDCN Is Associated with Loss of the Diphthamide Synthesis Pathway Enzyme DPH1 and Is Reversible By Azacitidine", 59th Annual Meeting of the American-Society-of-Hematology (ASH), pp. 1-8 (2017).
Chen et al., "NLLSS: Predicting Synergistic Drug Combinations Based on Semi-supervised Learning," PLOS Computational Biology, 12(7):e1004975, DOI:10.1371/journal.pcbi.1004975, pp. 1-23 (2016).
Daver, N. et al., "Ruxolitinib (RUX) in Combination with 5-Azacytidine (AZA) As Therapy for Patients (pts) with Myelofibrosis (MF)", Blood, 128(22): 1127, 4 pages (2016).
Deshpande A. et al., "Kinase domain mutations confer resistance to novel inhibitors targeting JAK2V617F in myeloproliferative neoplasms", Leukemia. 26(4):708-15 (2012).
Lomaia et al., "Long-term outcome of CML patient with mutation T315I. Case report and literature review," КЛИНИЧ ЕСКАЯ ОНКОГЕМАТОЛОГИЯ (Breves communications—Kurze Mitteilungen), 4 pages; English translation of relevant sections (2010).

(Continued)

*Primary Examiner* — Gyan Chandra
(74) *Attorney, Agent, or Firm* — McNeill PLLC

(57) ABSTRACT

The present invention provides methods for treating or inhibiting a myeloproliferative neoplasm (MPN) in a subject in need thereof, comprising administering to the subject a diphtheria toxin-human interleukin-3 conjugate (DT-IL3) and one or more Jak inhibitors and/or one or more hypomethylating agents.

19 Claims, 8 Drawing Sheets
Specification includes a Sequence Listing.

(56) References Cited

OTHER PUBLICATIONS

Sorm et al., "5-Azacytidine, a New, Highly Effective Cancerostatic," Brevi comunicazioni (Breves Communications—Kurze Mitteilungen, Brief Reports), pp. 202-203, 2 pages (1964).

Anonymous: "Tagraxofusp and Decitabine for the Treatment of Chronic Myelomonocytic Leukemia" URL: https://clinicaltrials.gov/study/NCT05038592 [retrieved on Dec. 2, 2024], pp. 1-11 (2024).

Tannito et al., "Tagraxofusp Shows Promising Anti-Tumoral Efficacy in Preclinical in Vitro Models of Myelofibrosis, Both As a Single Agent and in Combination with Janus Kinase Inhibitors," Blood 142 (Suppl. 1):6329-6330 (2023).

Krishnan et al., "Evaluation of Tagraxofusp (SL-401) Alone and in Combination with Ruxolitinib for the Treatment of Myeloproliferative Neoplasms," 61st American Society of Hematology Annual Meeting & Exposition (Dec. 7-10, 2019), 1 page.

Krishnan et al., "Evaluation of Tagraxofusp (SL-401) Alone and in Combination with Ruxolitinib for the Treatment of Myeloproliferative Neoplasms," Blood 134 (Suppl. 1): 2967 (Nov. 13, 2019).

Robilant et al., "Tagraxofusp Exhibits Antitumoral Activity in Preclinical Models of Myelofibrosis and Enhances Antileukemic Activity of JAK Inhibitors," Poster Presentation, European Hematology Association (EHA) 2024, 419092, Abstract P1005 (May 14, 2024) (2 pages).

Assi et al., "A phase II trial of ruxolitinib in combination with azacytidine in myelodysplastic syndrome/myeloproliferative neoplasms," Am J Hematol. 93; pp. 277-285 (2018).

Frankel et al., "Activity of SL-401, a targeted therapy directed to interleukin-3 receptor, in blastic plasmacytoid dendritic cell neoplasm patients," Blood 124(3), pp. 385-392 (2014).

Frolova et al., "SL-401 and SL-501, Targeted Therapeutics Directed at the Interleukin-3 Receptor, Inhibit the Growth of Leukaemic Cells and Stem Cells in Advanced Phase Chronic Myeloid Leukaemia," Br J Haematol. 66(6); pp. 862-874 (2014).

Masarova et al., "A phase 2 study of ruxolitinib in combination with azacitidine in patients with myelofibrosis," Blood 132(16); pp. 1664-1674 (2018).

```
                              SEQUENCE LISTING

<160> NUMBER OF SEQ ID NOS: 3

<210> SEQ ID NO 1
<211> LENGTH: 152
<212> TYPE: PRT
<213> ORGANISM: Homo sapiens

<400> SEQUENCE: 1

Met Ser Arg Leu Pro Val Leu Leu Leu Leu Gln Leu Leu Val Arg Pro
1               5                   10                  15

Gly Leu Gln Ala Pro Met Thr Gln Thr Thr Ser Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150

<210> SEQ ID NO 2
<211> LENGTH: 560
<212> TYPE: PRT
<213> ORGANISM: Corynebacterium diphtheriae

<400> SEQUENCE: 2

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
```

```
            50                  55                  60
Ser Gly Thr Gln Gly Asn Tyr Asp Asp Asp Trp Lys Gly Phe Tyr Ser
 65                  70                  75                  80

Thr Asp Asn Lys Tyr Asp Ala Ala Gly Tyr Ser Val Asp Asn Glu Asn
                 85                  90                  95

Pro Leu Ser Gly Lys Ala Gly Val Val Lys Val Thr Tyr Pro Gly
                100                 105                 110

Leu Thr Lys Val Leu Ala Leu Lys Val Asp Asn Ala Glu Thr Ile Lys
                115                 120                 125

Lys Glu Leu Gly Leu Ser Leu Thr Glu Pro Leu Met Glu Gln Val Gly
                130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Val Glu Tyr Ile Asn
                165                 170                 175

Asn Trp Glu Gln Ala Lys Ala Leu Ser Val Glu Leu Glu Ile Asn Phe
                180                 185                 190

Glu Thr Arg Gly Lys Arg Gly Gln Asp Ala Met Tyr Glu Tyr Met Ala
                195                 200                 205

Gln Ala Cys Ala Gly Asn Arg Val Arg Arg Ser Val Gly Ser Ser Leu
                210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
                260                 265                 270

Glu Glu Phe His Gln Thr Ala Leu Glu His Pro Glu Leu Ser Glu Leu
                275                 280                 285

Lys Thr Val Thr Gly Thr Asn Pro Val Phe Ala Gly Ala Asn Tyr Ala
                290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
                340                 345                 350

Ile Val Ala Gln Ser Ile Ala Leu Ser Ser Leu Met Val Ala Gln Ala
                355                 360                 365

Ile Pro Leu Val Gly Glu Leu Val Asp Ile Gly Phe Ala Ala Tyr Asn
                370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Leu His
                405                 410                 415

Asp Gly Tyr Ala Val Ser Trp Asn Thr Val Glu Asp Ser Ile Ile Arg
                420                 425                 430

Thr Gly Phe Gln Gly Glu Ser Gly His Asp Ile Lys Ile Thr Ala Glu
                435                 440                 445

Asn Thr Pro Leu Pro Ile Ala Gly Val Leu Leu Pro Thr Ile Pro Gly
                450                 455                 460

Lys Leu Asp Val Asn Lys Ser Lys Thr His Ile Ser Val Asn Gly Arg
465                 470                 475                 480
```

```
Lys Ile Arg Met Arg Cys Arg Ala Ile Asp Gly Asp Val Thr Phe Cys
                485                 490                 495

Arg Pro Lys Ser Pro Val Tyr Val Gly Asn Gly Val His Ala Asn Leu
            500                 505                 510

His Val Ala Phe His Arg Ser Ser Ser Glu Lys Ile His Ser Asn Glu
        515                 520                 525

Ile Ser Ser Asp Ser Ile Gly Val Leu Gly Tyr Gln Lys Thr Val Asp
    530                 535                 540

His Thr Lys Val Asn Ser Lys Leu Ser Leu Phe Phe Glu Ile Lys Ser
545                 550                 555                 560

<210> SEQ ID NO 3
<211> LENGTH: 388
<212> TYPE: PRT
<213> ORGANISM: Corynebacterium diphtheriae

<400> SEQUENCE: 3

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
```

-continued

```
           290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
        370                 375                 380

Lys Thr Arg Pro
385
```

COMBINATION THERAPY METHOD OF TREATING MYELOPROLIFERATIVE NEOPLASMS WITH A DIPHTHERIA TOXIN-HUMAN INTERLEUKIN-3 CONJUGATE IN COMBINATION WITH OTHER AGENTS

CROSS REFERENCE TO RELATED APPLICATIONS

This application is a national phase entry pursuant to 35 U.S.C. § 371 of International Application No. PCT/US2019/058769, filed Oct. 30, 2019, which claims the benefit of priority to U.S. Provisional Application Ser. No. 62/753,145, filed Oct. 31, 2018, and U.S. Provisional Application Ser. No. 62/832,558, filed Apr. 11, 2019, the contents of each of which are hereby incorporated by reference in their entireties.

SEQUENCE LISTING

[02] The present application is filed with a Sequence Listing in electronic format. The Sequence Listing is provided as a file entitled "2021-04-16_SeqList_ST25" created on Apr. 16, 2021, which is 10,070 bytes in size. The information in the electronic format of the sequence listing is incorporated herein by reference in its entirety.

DESCRIPTION

Field

The present invention provides methods for treating or inhibiting a myeloproliferative neoplasm (MPN) in a subject in need thereof. The method comprises administering to the subject a diphtheria toxin-human interleukin-3 conjugate (DT-IL3) and one or more Jak inhibitors and/or one or more hypomethylating agents.

Background

Myeloproliferative neoplasms (MPNs), also known as myeloproliferative diseases (MPDs), are hematological diseases characterized by excess production of bone marrow cells. MPNs are also characterized by clonal expansion of one or more hematopoietic cell lineages in the bone marrow. In some cases, a genetic mutation, such as mutation in the Jak2 protein, may be present in stem cells from a patient with an MPN.

MPNs may lead to increases in certain blood cells, abnormal blood cells, and enlargement of the spleen (splenomegaly). MPNs may damage the bone marrow and result in bone marrow fibrosis (myelofibrosis or MF). Anemia, fatigue, and weakness may occur due to changes in blood cell counts in MPN. Thrombohemorrhagic complications, such as thrombosis, are also a risk of MPN. Progression of MPNs can lead to development of further conditions, such as acute myeloid leukemia.

The present application describes improved methods for treating MPNs with a diphtheria toxin-human interleukin-3 conjugate (DT-IL3) and one or more Jak inhibitors and/or one or more hypomethylating agents.

SUMMARY

In accordance with the description, this application describes methods of treatment with a DT-IL3 and (a) one or more Jak inhibitors and/or (b) one or more hypomethylating agents.

In one embodiment, the present application provides a method for treating or inhibiting a myeloproliferative neoplasm (MPN) in a subject in need thereof, comprising administering to the subject a diphtheria toxin-human interleukin-3 conjugate (DT-IL3) and a) one or more Jak inhibitors and/or b) one or more hypomethylating agents.

In some embodiments, the DT-IL3 is administered at a dose of 1 p[μg/kg or greater, 2 μg/kg or greater, or 4 μg/kg or greater. In some embodiments, the DT-IL3 is administered at a dose of 2 μg/kg to 20 μg/kg or 9 μg/kg to 20 μg/kg. In some embodiments, the DT-IL3 is administered at a dose of 4 μg/kg to 12 μg/kg or 9 μg/kg to 12 μg/kg. In some embodiments, the DT-IL3 is administered at a dose of 5, 7, 9, or 12 μg/kg. In some embodiments, the DT-IL3 is administered at a dose that is the maximum tolerated dose.

In some embodiments, the DT-IL3 and the one or more Jak inhibitors and/or hypomethylating agents are administered at least one time a week. In some embodiments, the DT-IL3 and the one or more Jak inhibitors and/or hypomethylating agents are administered at least two times a week. In some embodiments, the DT-IL3 and one or more Jak inhibitors and/or hypomethylating agents are administered at least three times a week.

In some embodiments, the DT-IL3 and the (a) one or more Jak inhibitors and/or (b) one or more hypomethylating agents are administered over a period of one week or more. In some embodiments, the DT-IL3 and the (a) one or more Jak inhibitors and/or (b) one or more hypomethylating agents are administered over a period of two weeks or more.

In some embodiments, the DT-IL3 and the (a) one or more Jak inhibitors and/or (b) one or more hypomethylating agents are administered for at least 3 consecutive days.

In some embodiments, the DT-IL3 and the (a) one or more Jak inhibitors and/or (b) one or more hypomethylating agents are administered in multiple treatment cycles. In some embodiments, the treatment cycles are at least 1 week apart, at least 2 weeks apart, at least 3 weeks apart, at least 4 weeks apart, at least 5 weeks apart, or a combination thereof.

In some embodiments, the DT-IL3 is administered for at least 3 consecutive days every 21 days for four cycles, followed by every 28 days for 3 cycles, and then every 42 days.

In some embodiments, the one or more Jak inhibitors are administered at least once daily, or at least twice daily.

In some embodiments, the one or more hypomethylating agents are administered for at least the first 3 days, at least the first 4 days, at least the first 5 days, at least the first 6 days, or at least the first 7 days of at least one cycle.

In some embodiments, the one or more hypomethylating agents are administered for at least the first 3 days, at least the first 4 days, at least the first 5 days, at least the first 6 days, or at least the first 7 days of a 28-day cycle for 3 cycles following administration of DT-IL3 for four 21-day cycles.

The method of any one of the preceding claims, wherein the DT-IL3 and the (a) one or more Jak inhibitors and/or (b) one or more hypomethylating agents are administered until disease progression and/or unacceptable toxicity is obtained.

In some embodiments, the subject is administered a pharmaceutical composition comprising the DT-IL3 and the (a) one or more Jak inhibitors and/or (b) one or more hypomethylating agents.

In some embodiments, the subject is human. In some embodiments, the human has unfavorable cytogenetics.

In some embodiments, the DT-IL3 is a chemical conjugate.

In some embodiments, the DT-IL3 is a recombinantly expressed protein.

In some embodiments, the DT-IL3 is expressed as a single polypeptide comprising the catalytic and translocation domains of diphtheria toxin and human IL-3. In some embodiments, the DT-IL3 expressed as a single polypeptide comprising the catalytic and translocation domains of diphtheria toxin comprises the amino acid sequence of SEQ ID NO:3 and/or the human IL-3 comprises the amino acid sequence of SEQ ID NO:1.

In some embodiments, the DT-IL3 comprises amino acid residues 1 to 388 of diphtheria toxin linked via a peptide bond to human IL-3. In some embodiments the diphtheria toxin has an amino acid sequence of SEQ ID NO:2 and/or human IL-3 has an amino acid sequence of SEQ ID NO:1.

In some embodiments, the inhibition results in a reduction in the proliferation of MPN cells, a stabilization in the amount of MPN cells, and/or a reduction in the amount of MPN cells.

In some embodiments, the inhibition results in a reduction in spleen and/or liver size.

In some embodiments, the MPN is polycythemia vera, essential thrombocytosis, myelofibrosis, chronic myelomonocytic leukemia, chronic neutrophilic leukemia, chronic eosinophilic leukemia, systemic mastocytosis, symptomatic hypereosinophilic disorder, or other bone marrow disorder that causes the production of excess red blood cells, white blood cells, and/or platelets. In some embodiments, the MPN is myelofibrosis. In some embodiments, the myelofibrosis is primary myelofibrosis, post-polycythemia vera myelofibrosis, post-essential thrombocythemia myelofibrosis, blast phase primary myelofibrosis, post-polycythemia vera myelofibrosis in blast phase, or post-ET myelofibrosis in blast phase.

In some embodiments, the MPN is in blast phase.

In some embodiments, the MPN is primary myelofibrosis in blast phase, post-polycythemia vera myelofibrosis in blast phase, or post-ET myelofibrosis in blast phase.

In some embodiments, the one or more Jak inhibitors comprises ruxolitinib.

In some embodiments, the one or more hypomethylating agents comprise azacitidine, decitabine, and/or SGI-110.

In some embodiments, at least one Jak inhibitor and at least one hypomethylating agent is administered.

In some embodiments, the at least one Jak inhibitor comprises ruxolitinib and the at least one hypomethylating agent comprises decitabine, azacitidine, and/or SGI-110.

In some embodiments, the subject was refractory to prior treatment with one or more Jak inhibitors and/or one or more hypomethylating agents. In some embodiments, the subject was refractory to prior treatment with the Jak inhibitor ruxolitinib. In some embodiments, the subject has MF.

In some embodiments, the subject could not tolerate the full dose of a prior treatment with one or more Jak inhibitors and/or one or more hypomethylating agents. In some embodiments, the subject could not tolerate the full dose of a prior treatment with the Jak inhibitor ruxolitinib. In some embodiments, the subject has MF.

In some embodiments, the subject has low platelet counts or was not eligible for treatment with ruxolitinib. In some embodiments, the subject has MF.

In some embodiments, the subject previously responded to a Jak inhibitor and/or a hypomethylating agent. In some embodiments, the subject has MF.

In some embodiments, the subject has mutations in the JAK2, MPL, ASXL1, TET2, or CALR gene. In some embodiments, the subject has the JAK2V617F mutation.

Also provided herein are pharmaceutical compositions for treating or inhibiting a myeloproliferative neoplasm (MPN) in a subject in need thereof comprising an effective amount of a diphtheria toxin-human interleukin-3 conjugate (DT-IL3) and one or more Jak inhibitors and/or one or more hypomethylating agents. In some embodiments, the pharmaceutical composition further comprises a pharmaceutically acceptable excipient.

Also provided herein are methods for treating a myeloproliferative neoplasm (MPN) in a subject in need thereof, comprising: a) identifying the MPN, and b) administering an effective amount of a diphtheria toxin-human interleukin-3 conjugate (DT-IL3) and one or more Jak inhibitors and/or one or more hypomethylating agents to the subject in need thereof.

In some embodiments, the MPN is identified by physical examination, blood tests, bone marrow aspirate and biopsy, cytogenetic analysis, testing for mutations in the JAK2, MPL, ASXL1, TET2, or CALR gene, arterial oxygen saturation and carboxyhaemoglobin levels, neutrophil alkaline phosphatase levels, vitamin B12 or B12 binding capacity, or serum urate.

In some embodiments, the MPN is identified by testing for the JAK2V617F mutation.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

DESCRIPTION OF THE FIGURES

FIG. 1A shows the mean fluorescence intensity of CD123 on CMML blasts, monocytes, and lymphocytes. FIG. 1B shows the mean fluorescence intensity CD123 on CMML blasts and monocytes normalized to the mean fluorescence intensity of CD123 on lymphocytes. FIGS. 1C and 1D show the mean fluorescence intensity of CD123 on blasts (FIG. 1C) and monocytes (FIG. 1D) by different CMML subtypes, CMML-0, CMML-1, and CMML-2. Results are normalized to the mean fluorescence intensity of CD123 on lymphocytes. FIG. 1E shows the percentage of CD123-positive blasts in CMML subtypes CMML-1 and CMML-2. Overall, FIGS. 1A-1E demonstrate that CD123 is highly expressed on blasts and monocytes relative to lymphocytes in CMML patients.

In FIG. 3A, cells were exposed to increasing concentrations of AZA or the combination of AZA and DT-IL3. In FIG. 3B, cells were exposed to 1 µM AZA, 4.8 nM DT-IL3, or the combination of 1 µM AZA and 4.8 nM DT-IL3. Overall, FIGS. 3A-3B show that AZA and DT-IL3 significantly reduced cell viability of primary CMML mononuclear cells when compared to AZA alone.

FIGS. 4A-4D show results from cells of individual patient. In FIGS. 4A-4C, cells were exposed to AZA (1, 5, or 10 µM) alone or the combination of 1 µM AZA and DT-IL-3 (2.5 or 10 nM). Addition of 10 nM of DT-IL3 to 1 µM AZA led to a significant reduction in colony formation. In FIG. 4D, cells were exposed to DT-IL3 (2.5, 10, or 20 nM) alone or the combination of 10 nM DT-IL3 and AZA (1 or 2.5 µM). Addition of AZA to DT-IL3 led to a significant reduction in colony formation. Overall, FIGS. 4A-4D show that AZA and DT-IL3 significantly reduced colony formation of CMML mononuclear cells when compared to AZA or DT-IL3 alone.

DESCRIPTION OF THE SEQUENCES

Figure 1B:
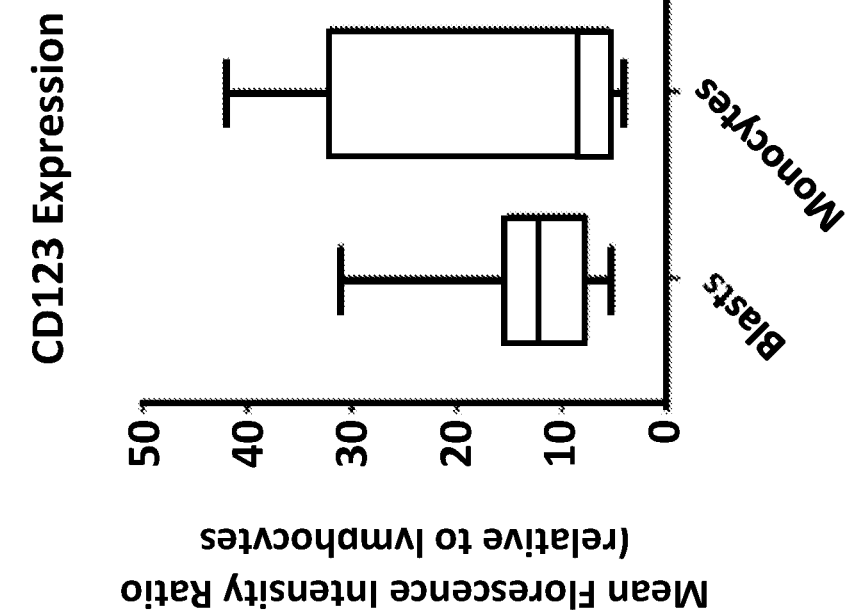
FIGS. 1A-1E show expression of CD123 on blasts and monocytes in chronic myelomonocytic leukemia (CMML) patients (N=20) as assessed by flow cytometry. Lymphocyte CD123 expression was used as a control.
Figure 1A:
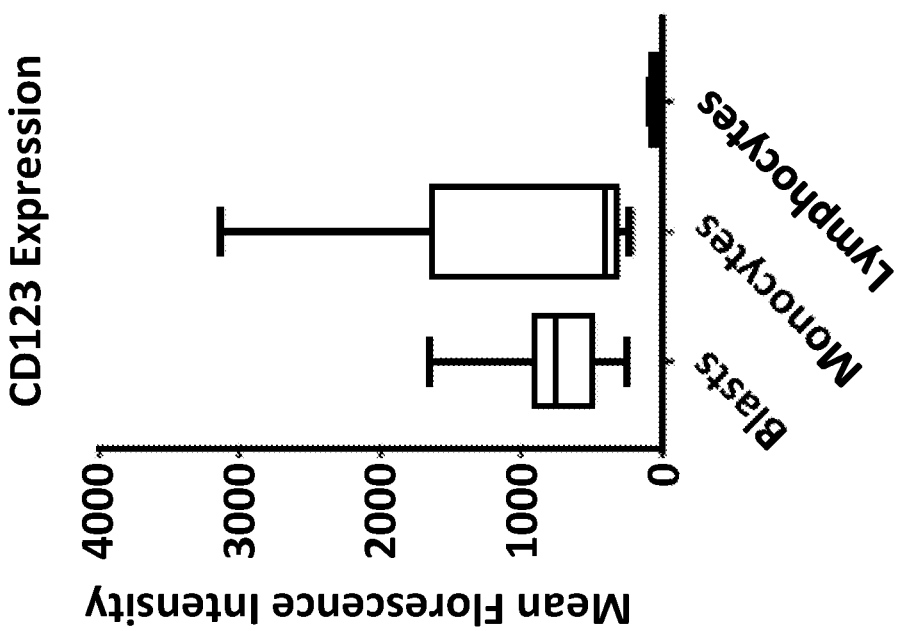
Figure 1D:
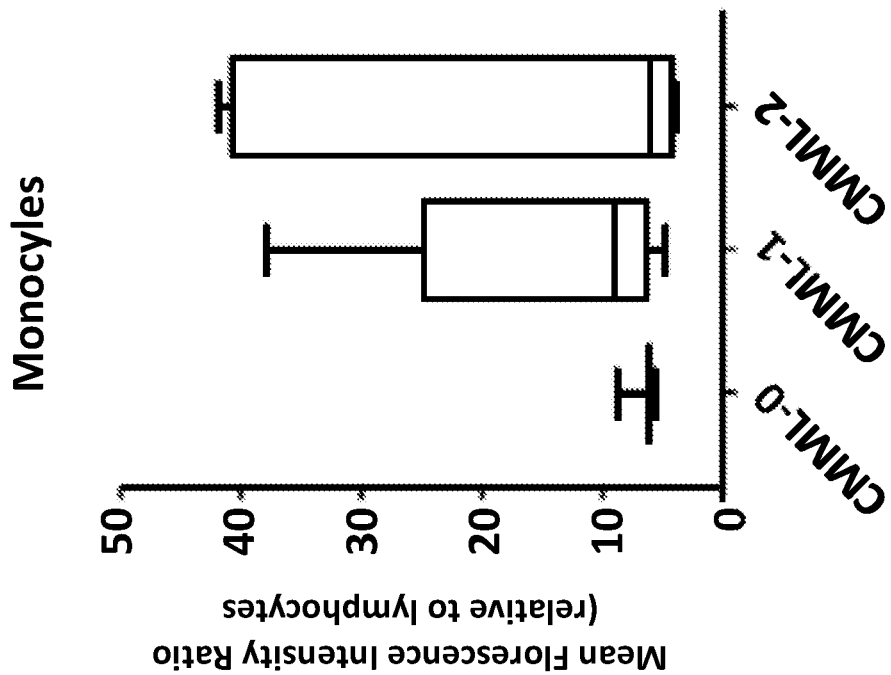
Figure 1C:
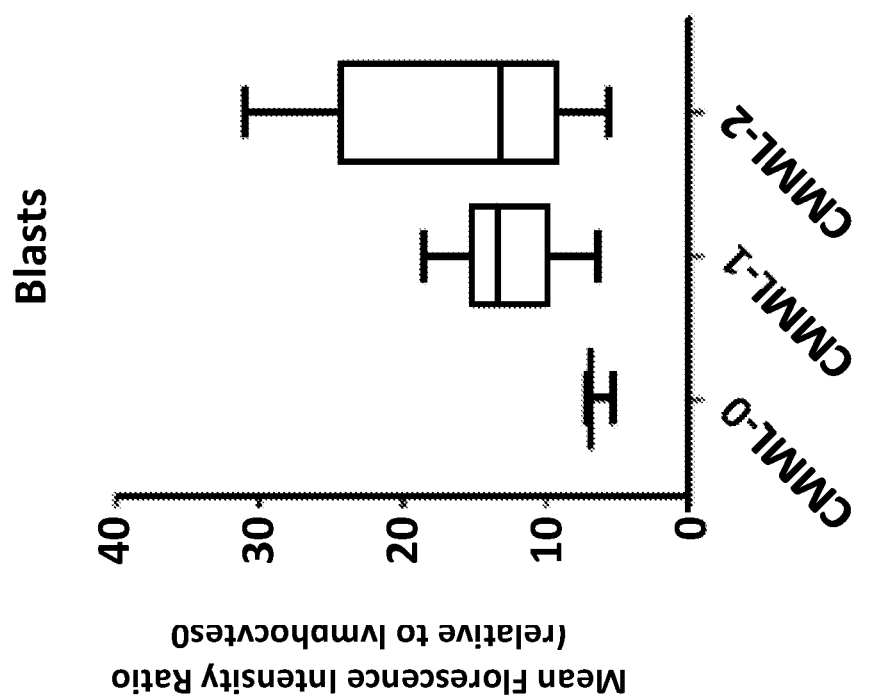
Figure 1E:
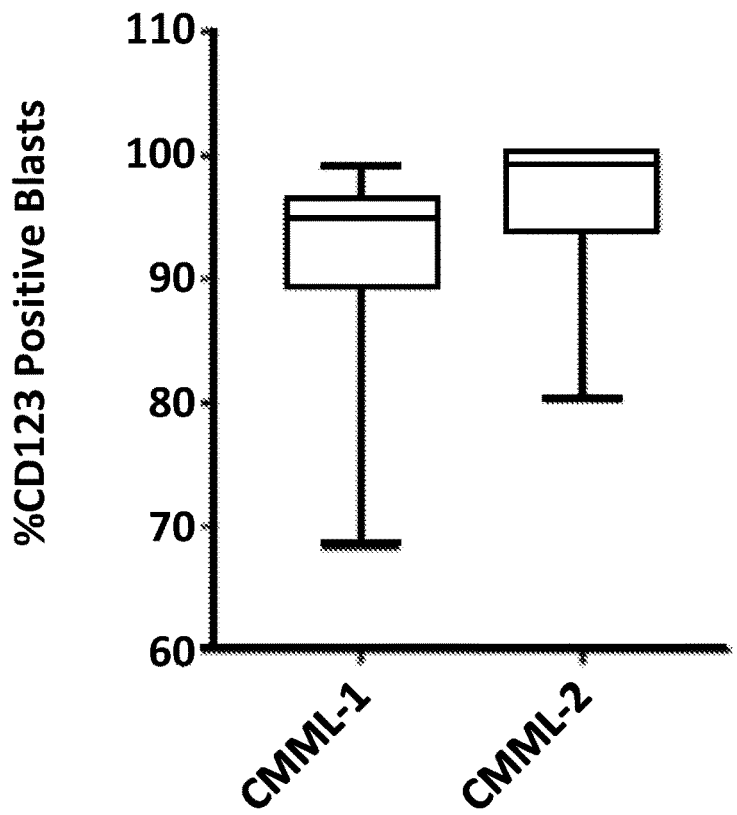

Table 1 provides a listing of certain sequences referenced herein.

prises the DT-IL3 and the (a) one or more Jak inhibitors and/or (b) one or more hypomethylating agents.

In some embodiments, the DT-IL3 and the (a) one or more Jak inhibitors and/or (b) one or more hypomethylating agents are administered separately. In some embodiments, the DT-IL3 and the (a) one or more Jak inhibitors and/or (b) one or more hypomethylating agents are administered at different times or on different days.

A. Diphtheria Toxin-Human Interleukin-3 Conjugate (DT-IL3)

"DT-IL3" refers to a conjugate of human interleukin-3 (IL-3) and diphtheria toxin (DT). DT-IL-3 conjugates are known in the art and their administration in accordance with the methods of the present disclosure are contemplated herein. For example, DT-IL-3 conjugates described in U.S. Pat. Nos. 7,763,242; 8,470,307; 9,181,317; 9,631,006, and WO2008/030539 may be used in accordance with the methods disclosed by the present invention. These references are incorporated by reference in their entirety for their disclosure of DT-IL3. See also, e.g., the conjugates of Liu et al. Exp. Hematol. 32:277-281 (2004); Hogge et al. Clin. Cancer Res. 12:1284-1291 (2006); Testa et al. Blood 106:2527-2529 (2005); and Klein et al. Biochem. Biophys. Res. Comm. 288:1244-1249 (2001)), also incorporated by reference in their entirety.

In certain embodiments, the conjugate comprises the catalytic and translocation domains of diphtheria toxin fused

TABLE 1

Description of the Sequences

| Description | | Sequences | | | | SEQ ID NO |
|---|---|---|---|---|---|---|
| Human IL-3 | 1 | MSRLPVLLLL | QLLVRPGLQA | PMTQTTSLKT | SWVNCSNMID EIITHLKQPP LPLLDFNNLN | 1 |
| | 61 | GEDQDILMEN | NLRRPNLEAF | NRAVKSLQNA | SAIESILKNL LPCLPLATAA PTRHPIHIKD | |
| | 121 | GDWNEFRRKI | TFYLKTLENA | QAQQTTLSLA | IF | |
| Diphtheria toxin (DT) | 1 | MSRKTFASIL | IGALLGIGAP | PSAHAGADDV | VDSSKSFVME NFSSYHGTKP GYVDSIQKGI | 2 |
| | 61 | QKPKSGTQGN | YDDDWKGFYS | TDNKYDAAGY | SVDNENPLSG KAGGVVKVTY PGLTKVLALK | |
| | 121 | VDNAETIKKF | LGLSLTEPLM | EQVGTEEFIK | RFGDGASRVV LSLPFAEGSS SVEYINNWEQ | |
| | 181 | AKALSVELEI | NFETRGKRGQ | DAMYEYMAQA | CAGNRVRRSV GSSLSCINLD WDVIRDKTKT | |
| | 241 | KIESLKPHGP | IKNKMSESPN | KTVSEEKAKQ | YLEEFHQTAL EHPELSELKT VTGTNPVFAG | |
| | 301 | ANYAAWAVNV | AQVIDSETAD | NLEKITAALS | ILPGIGSVMG IADGAVHHNT EEIVAQSIAL | |
| | 461 | SSLMVAQAIP | LVGELVDIGF | AAYNFVESII | NLFQVVHNSY NRPAYSPGHK TQPFLHDGYA | |
| | 421 | VSWNTVEDSI | IRTGFQGESG | HDIKITAENT | PLPIAGVLLP TIPGKTDVNK SKTHISVNGR | |
| | 481 | KIRMRCRAID | GDVTFCRPKS | PVYVGNGVHA | NLHVAFHRSS SEKIHSNEIS SDSIGVLGYQ | |
| | 541 | KTVDHTKVNS | KTSLFFEIKS | | | |
| Catalytic and translocation domains of DT | 1 | GADDVVDSSK | SFVMENFSSY | HGTKPGYVDS | IQKGIQKPKS GTQGNYDDDW KGFYSTDNKY | 3 |
| | 61 | DAAGYSVDNE | NPLSGKAGGV | VKVTYPGLTK | VLALKVDNAE TIKKFLGLSL TEPLMEQVGT | |
| | 121 | EEFIKRFGDG | ASRVVLSLPF | AEGSSSVEYI | NNWEQAKALS VELEINFETR GKRGQDAMYE | |
| | 181 | YMAQACAGNR | VRRSVGSSLS | CINLDWDVIR | DKTKTKIESL KFHGPIKNKM SESPNKTVSE | |
| | 241 | EKAKQYLEEF | HQTALEHPEL | SELKTVTGTN | PVFAGANYAA WAVNVAQVID SETADNLEKT | |
| | 301 | TAALSILPGI | GSVMGIADGA | VHHNTEEIVA | QSIALSSLMV AQAIPLVGEL VDIGFAAYNF | |
| | 361 | VESIINLFQV | VHNSYNRPAY | SPGHKTRP | | |

DESCRIPTION OF THE EMBODIMENTS

I. Agents for Treatment

This application provides methods of treatment of a myeloproliferative neoplasm (MPN) comprising administering a diphtheria toxin-human interleukin-3 conjugate (DT-IL3) and (a) one or more Jak inhibitors and/or (b) one or more hypomethylating agents to a subject.

In some embodiments, the DT-IL3 and the (a) one or more Jak inhibitors and/or (b) one or more hypomethylating agents are administered at the same time or on the same day. In some embodiments, a pharmaceutical composition comvia a covalent bond to human IL-3. In other embodiments, the diphtheria toxin is linked via a peptide linker to the human IL-3 portion of the conjugate. The linker for the conjugate may be, for example, two, three, four, five, ten, up to fifteen, or fifteen amino acids in length. The length of the linker may vary to provide optimal binding of the conjugate. In some embodiments, the peptide linker is two to four amino acids long. The peptide linker may be a His-Met linker Although not intending to be bound by a particular mechanism of action, the flexible peptide linker facilitates chain pairing and minimizes possible refolding. Linker molecules are commonly known in the art and described in Denardo et al., 1998, Clin. Cancer Res. 4:2483-90; Peterson et al, 1999, *Bioconjug. Chem.* 10:553; and Zimmerman et al., 1999, *Nucl. Med. Biol.* 26:943-50 each incorporated by reference in their entireties.

In some embodiments, the application provides pharmaceutical compositions that include a DT-IL3 of the invention and a pharmaceutically acceptable carrier. In accordance with the present invention, the conjugate can include any domain of DT linked via any linker molecule known in the art to any domain of IL-3. In certain embodiments, the conjugate is DT$_{388}$IL-3, which is a fusion protein of an N-terminal methionine, followed by amino acids 1-388 of DT fused to full-length, mature, human IL-3 via a His-Met amino acid linker.

In some embodiments, DT-IL3 mediates selective targeting to cells expressing the interleukin-3 receptor (IL-3 receptor). In some embodiments, DT-IL3 targets to MPN cells expressing the IL-3 receptor. In some embodiments, DT-IL3 targets tumor-promoting cells (such as IL-3R+ plasmacytoid dendritic cells) in the tumor microenvironment.

1. IL-3

Interleukin-3 (IL-3) is a cytokine that supports the proliferation and differentiation of multi-potential and committed myeloid and lymphoid progenitors. See, e.g., Nitsche et al. *Stem Cells* 21: 236-244 (2003). IL-3 may also be referred to as hematopoietic growth factor, mast cell growth factor (MCGF), multipotential colony-stimulating factor, or P-cell-stimulating factor.

In some embodiments, the DT-IL3 conjugates include the full-length, mature (lacking the signal peptide) interleukin-3 protein (IL-3), or a portion, analog or derivative thereof that binds to the interleukin-3 receptor or a subunit thereof expressed on a cell surface, conjugated through a recombinant technology or through chemical (covalent) bond to diphtheria toxin or a portion, analog or derivative thereof, which toxin lacks the native cell binding domain.

Fragments, analogs, and derivatives of IL-3 can be useful in the present invention provided that when fused to the DT portion of the conjugate, such fragments, analogs and derivatives maintain the ability to bind a subunit of the IL-3 receptor or the native IL-3 receptor expressed on the surface of a cell. The binding kinetics of the fragments, analogs or derivatives may remain the same or vary only by not more than 25%. The IL-3 polypeptide may be from any species. In certain embodiments, the IL-3 is a mammalian IL-3, e.g., an IL-3 polypeptide is human IL-3, an analog, derivative, or a fragment thereof.

In some embodiments, the IL-3 is human IL-3. An exemplary amino acid sequence of human IL-3 can be found in the GenBank database (see, e.g., Accession No. AAC08706) or UniProt #P08700. An exemplary amino acid sequence of human IL-3 is:

```
                                         [SEQ ID NO: 1]
    msrlpvllll  qllvrpglqa  pmtqttslkt  swvncsnmid eiithlkqpp  lplldfnnln  gedqdilmen  nlrrpnleaf nravkslqna  saiesilknl  lpclplataa  ptrhpihikd gdwnefrrkl  tfylktlena  qaqqttlsla  if.
```

In some embodiments, IL-3 is at least 50%, at least 65%, at least 70%, at least 75%, at least 80%, at least 85%, at least 90%, or at least 95%, at least 96%, at least 97%, at least 98%, or at least 99% identical to SEQ ID NO: 1.

2. Diphtheria Toxin

Diphtheria toxin (DT) is a protein with three domains: a catalytic domain (amino acids 26-112; underlined sequence within SEQ ID NO: 1 below) connected by an arginine-rich disulfide loop to a translocation domain (amino acids 225-404; italicized sequence within SEQ ID NO:1) followed by a cell binding domain (amino acids 406-559). An exemplary amino acid sequence of DT, accessible from GenBank Accession No. AOU74567.1 or UniProt #A0A142BWN1 is:

```
                                         [SEQ ID NO: 2]
    MSRKLFASIL  IGALLGIGAP  PSAHAGADDV  VDSSKSFVME

NFSSYHGTKP  GYVDSIQKGIQKPKSGTQGN  YDDDWKGFYS

TDNKYDAAGY  SVDNENPLSG  KAGGVVKVTY  PGLTKVLALK

VDNAETIKKE  LGLSLTEPLM  EQVGTEEFIK  RFGDGASRVV

LSLPFAEGSS  SVEYINNWEQ  AKALSVELEI  NFETRGKRGQ

DAMYEYMAQA  CAGNRVRRSV  GSSLSCINLD  WDVIRDKTKT

KIESLKEHGP  IKNKMSESPN  KTVSEEKAKQ  YLEEFHQTAL

EHPELSELKT  VTGTNPVFAG  ANYAAWAVNV  AQVIDSETAD

NLEKTTAALS  ILPGIGSVMG  IADGAVHHNT  EEIVAQSIAL

SSLMVAQAIP  LVGELVDIGF  AAYNFVESII  NLFQVVHNSY

NRPAYSPGHK  TQPFLHDGYA  VSWNTVEDSI  IRTGFQGESG

HDIKITAENT  PLPIAGVLLP  TIPGKLDVNK  SKTHISVNGR

KIRMRCRAID  GDVTFCRPKS  PVYVGNGVHA  NLHVAFHRSS

SEKIHSNEIS  SDSIGVLGYQ  KTVDHTKVNS  KLSLFFEIKS.
```

Fragments, analogs and derivatives of DT can be useful in the present application. In some embodiments, DT consists of the catalytic, the translocation, and the cell binding domains of DT. In some embodiments, DT consists of the cell binding and the catalytic domains of DT. In some embodiments, DT consists of the cell binding and the translocation domains of DT. In some embodiments, DT consists of the catalytic and translocation domains of DT. In some embodiments, DT comprises one of the translocation, catalytic, or cell binding domain.

The DT fragment conjugated to the IL-3 is the catalytic domain and the translocation domain of DT, represented by exemplary SEQ ID NO: 3:

```
                                         [SEQ ID NO: 3]
    GADDVVDSSK  SFVMENFSSY  HGTKPGYVDS  IQKGIQKPKS

GTQGNYDDDW  KGFYSTDNKY  DAAGYSVDNE  NPLSGKAGGV

VKVTYPGLTK  VLALKVDNAE  TIKKELGLSL  TEPLMEQVGT

EEFIKRFGDG  ASRVVLSLPF  AEGSSSVEYI  NNWEQAKALS

VELEINFETR  GKRGQDAMYE  YMAQACAGNR  VRRSVGSSLS

CINLDWDVIR  DKTKTKIESL  KEHGPIKNKM  SESPNKTVSE

EKAKQYLEEF  HQTALEHPEL  SELKTVTGTN  PVFAGANYAA

WAVNVAQVID  SETADNLEKT  TAALSILPGI  GSVMGIADGA

VHHNTEEIVA  QSIALSSLMV  AQAIPLVGEL  VDIGFAAYNF

VESIINLFQV  VHNSYNRPAY  SPGHKTRP.
```

In some embodiments, the DT fragment is at least 50%, at least 65%, at least 70%, at least 75%, at least 80%, at least 85%, at least 90%, or at least 95%, at least 96%, at least 97%, at least 98%, or at least 99% identical to SEQ ID NO: 3.

3. Methods for Producing DT-IL3 Conjugates

The DT-IL3 conjugates of the present invention can be made by standard recombinant DNA techniques or by protein synthetic techniques, e.g., by use of a peptide synthesizer. For example, a nucleic acid molecule encoding a conjugate of the invention can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al., eds., John Wiley & Sons, 1992).

The nucleotide sequences encoding a conjugate of the invention (IL-3 and diphtheria toxin sequences) may be obtained from any information available to those of skill in the art (i.e., from GenBank, the literature, or by routine cloning). The nucleotide sequence coding for a conjugate can be inserted into an appropriate expression vector, i.e., a vector which contains the necessary elements for the transcription and translation of the inserted protein-coding sequence. In some instances, the diphtheria toxin sequence can be truncated in order to remove a specific domain, such as the targeting domain. The techniques for modifying or truncating DNA are well known to those of skill in the art of molecular biology. Also, the IL-3 and the diphtheria toxin sequences can be ligated in such a way as to generate a DNA sequence that, when translating, creates a polypeptide that is a compound of the invention. In some embodiments, a linker sequence is introduced into the recombinant sequence that links the IL-3 sequence and the diphtheria toxin sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast (e.g., Pichia) containing yeast vectors; or bacteria (such as *E. coli*) transformed with bacteriophage, DNA, plasmid DNA, or cosmid DNA. The expression elements of vectors vary in their strengths and specificities. Depending on the host-vector system utilized, any one of a number of suitable transcription and translation elements may be used. In some embodiments, the protein is expressed in *E. coli*. In some embodiments, the protein is expressed in Pichia.

The expression of a conjugate of the invention may be controlled by any promoter or enhancer element known in the art. In some embodiments, the expression of a conjugate of the invention is regulated by a constitutive promoter. In another embodiment, the expression is regulated by an inducible promoter. In another embodiment, the expression is regulated by a tissue-specific promoter.

In some embodiments, a vector is used that comprises a promoter operably linked to a conjugate-encoding nucleic acid, one or more origins of replication and, optionally, one or more selectable markers (e.g., an antibiotic resistance gene).

Expression vectors containing inserts of a gene encoding a conjugate can be identified by three general approaches: (a) nucleic acid hybridization, (b) presence or absence of "marker" gene functions, and (c) expression of inserted sequences. In the first approach, the presence of a gene encoding a conjugate in an expression vector can be detected by nucleic acid hybridization using probes comprising sequences that are homologous to an inserted gene encoding the conjugate. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a conjugate in the vector. For example, if the nucleotide sequence encoding the conjugate is inserted within the marker gene sequence of the vector, recombinants containing the gene encoding the conjugate insert can be identified by the absence of the marker gene function. In the third approach, recombinant expression vectors can be identified by assaying the gene product (e.g., conjugate) expressed by the recombinant. Such assays can be based, for example, on the physical or functional properties of the conjugate in in vitro assay systems, e.g., binding to an antibody or the IL-3 receptor.

Recombinant conjugates may be stably expressed for long-term, high-yield production. For example, cell lines which stably express the conjugate of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express a conjugate of the invention.

The DT-IL3 is generally produced recombinantly, using bacterial, insect, or mammalian cells containing a nucleic acid engineered to express the conjugate protein, as described above.

Once a conjugate of the invention has been produced by recombinant expression or by chemical synthesis, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

B. Jak Inhibitors

As used herein, a "Jak inhibitor" is an agent that inhibits one or more Janus kinases (Jak). The Jak inhibitor can be any agent that inhibits one or more Jak, whether or not this agent has other pharmaceutical effects. Jak includes Jak1, Jak2, Jak3, and Tyk2. In some embodiments, the Jak inhibitor inhibits Jak1 or Jak2 In some embodiments, the Jak inhibitor is a Jak2/Jak1 inhibitor. In some embodiments, the Jak inhibitor may also inhibit other kinases.

Jaks mediate the signaling of certain cytokines and growth factors critical for hematopoiesis and immune function. In some embodiments, inhibition of one or more Jaks reduces splenomegaly and decreases circulating cytokine levels.

In some embodiments, the one or more Jak inhibitors comprises ruxolitinib, gandotinib, momelotinib, pacritinib, CHZ868, NS-018, SRC, tofacitinib, or itacitinib. In some embodiments, the Jak inhibitor used in accordance with some of the methods provided herein is ruxolitinib.

C. Hypomethylating Agents

As used herein, a "hypomethylating agent" is any drug that inhibits DNA methylation (i.e., the addition of a methyl group to a DNA nucleotide). The hypomethylating agent can be any agent that inhibits DNA methylation, whether or not this agent has other pharmaceutical effects.

In some embodiments, the hypomethylating agent blocks the activity of a DNA methyltransferase (i.e., the compound is a DNA methyltransferase inhibitor or DNMT inhibitor). In some embodiments, a hypomethylating agent decreases DNA methylation without causing substantial suppression of DNA synthesis. In some embodiments, a hypomethylating agent restores normal function to genes. In some embodiments, a hypomethylating agent causes death of rapidly dividing cells.

In some embodiments, the one or more hypomethylating agents comprise azacitidine, decitabine, and/or SGI-110.

D. Dosing

The agents of this invention may be dosed at any clinically relevant dose. By clinically relevant, it is meant that the dose of the agent has an effect in the subject. In some embodiments, the combinations of agents disclosed herein allow one or more agents to be dosed at a lower dosage level than the dose at which said agent would have an effect when dosed as a single agent. For example, treatment with DT-IL3 together with one or more Jak inhibitors and/or one or more hypomethylating agents provides clinically relevant effects that would not be seen for the same dose of Jak inhibitor or hypomethylating agent when dosed as a single-agent.

In some embodiments, one or more agents is dosed at the maximum tolerated dose. "Maximum tolerated dose," as used herein, refers to the highest dose of an agent that an individual patient can tolerate. In other words, side effects in a given patient can determine the maximum tolerated dose. Side effects may limit the ability to administer higher doses of a treatment than the maximum tolerated dose. Therefore, the maximum tolerated dose for a given patient may be lower than those indicated in the prescribing information for the treatment or those commonly used in clinical practice. The maximum tolerated dose may have limited or not clinical efficacy in a patient.

1. Exemplary Doses of DT-IL3

In some embodiments, the DT-IL3 is administered at a dose of 1 µg/kg or greater, 2 µg/kg or greater, or 4 µg/kg or greater. In some embodiments, DT-IL3 is administered at a dose of 2 µg/kg to 20 µg/kg or 9 µg/kg to 20 µg/kg. In some embodiments, the DT-IL3 is administered at a dose of 4 µg/kg to 12 µg/kg or 9 µg/kg to 12 µg/kg. In some embodiments, the DT-IL3 is administered at a dose of 5 µg/kg. In some embodiments, the DT-IL3 is administered at a dose of 7 µg/kg. In some embodiments, the DT-IL3 is administered at a dose of 9 µg/kg. In some embodiments, the DT-IL3 is administered at a dose of 12 µg/kg.

In some embodiments, the DT-IL3 is administered at a dose that is the maximum tolerated dose.

2. Exemplary Doses of Jak Inhibitors

In some embodiments, the one or more Jak inhibitors comprises ruxolitinib. In some embodiments, ruxolitinib is dosed at 0.5 mg, 1 mg, 2.5 mg, 5 mg, 10 mg, 15 mg, 20 mg, or 25 mg orally.

In some embodiments, gandotinib is dosed at 0.5 mg, 1 mg, 2.5 mg, 5 mg, 10 mg, 15 mg, 30 mg, 60 mg, 90 mg, or 120 mg orally.

In some embodiments, momelotinib is dosed at 0.5 mg, 1 mg, 2.5 mg, 5 mg, 10 mg, 25 mg, 50 mg, 75 mg, 100 mg, 150 mg, 200 mg, 300 mg, or 400 mg orally.

In some embodiments, pacritinib is dosed at 0.5 mg, 1 mg, 2.5 mg, 5 mg, 10 mg, 25 mg, 50 mg, 75 mg, 100 mg, 150 mg, 200 mg, 300 mg, or 400 mg orally.

In some embodiments, CHZ868 is dosed at 0.5 mg, 1 mg, 2.5 mg, 5 mg, 10 mg, 25 mg, 50 mg, 75 mg, 100 mg, 150 mg, 200 mg, 300 mg, or 400 mg orally.

In some embodiments, NS-018 is dosed at 0.5 mg, 1 mg, 2.5 mg, 5 mg, 10 mg, 15 mg, 25 mg, 50 mg, 75 mg, 100 mg, 150 mg, 200 mg, 300 mg, or 400 mg orally.

In some embodiments, SRC is dosed at 0.5 mg, 1 mg, 2.5 mg, 5 mg, 10 mg, 15 mg, 20 mg, 25 mg, 50 mg, 75 mg, 100 mg, 150 mg, 200 mg, 300 mg, or 400 mg orally.

In some embodiments, tofacitinib is dosed at 0.5 mg, 1 mg, 2.5 mg, 5 mg, 10 mg, 15 mg, 20 mg, 25 mg, or 30 mg orally.

In some embodiments, itacitinib is dosed at 0.5 mg, 1 mg, 2.5 mg, 5 mg, 10 mg, 15 mg, 20 mg, 25 mg, 50 mg, 75 mg, 100 mg, 150 mg, 200 mg, 300 mg, or 400 mg orally.

In some embodiments, the Jak inhibitor is administered at a dose that is the maximum tolerated dose.

3. Exemplary Doses of Hypomethylating Agents

In some embodiments, azacitidine (Vidaza®) is dosed at 75 mg/m$^2$ or less. In some embodiments, azacitidine is dosed at 1 mg/m$^2$, 2.5 mg/m$^2$, 5 mg/m$^2$, 10 mg/m$^2$, 15 mg/m$^2$, 20 mg/m$^2$, 25 mg/m$^2$, 37.5 mg/m$^2$, 50 mg/m$^2$, 75 mg/m$^2$, or 100 mg/m$^2$ by continuous intravenous infusion or subcutaneous injection.

In some embodiments, decitabine (Dacogen®) is dosed at 45 mg/m$^2$/day or less. In some embodiments, decitabine (Dacogen®) is dosed at 1 mg/m$^2$/day, 5 mg/m$^2$/day, 10 mg/m$^2$/day, 15 mg/m$^2$/day, 20 mg/m$^2$/day, 33 mg/m$^2$/day, or 45 mg/m$^2$/day. The infusion may be a single daily continuous intravenous infusion or multiple continuous intravenous infusions in a day.

In some embodiments, SGI-110 (guadecitabine) is dosed at 1 mg/m$^2$, 3 mg/m$^2$, 5 mg/m$^2$, 10 mg/m$^2$, 15 mg/m$^2$, 20 mg/m$^2$, 25 mg/m$^2$, 30 mg/m$^2$, or 60 mg/m$^2$ by subcutaneous injection.

In some embodiments, the hypomethylating agent is administered at a dose that is the maximum tolerated dose.

In some embodiments, the subject is premedicated for nausea and vomiting before administration of the hypomethylating agent.

II. Methods of Treatment

In some embodiments, a DT-IL3 is administered with (a) one or more Jak inhibitors and/or (b) one more hypomethylating agents for treatment of an MPN.

In some embodiments, a method of treatment comprises administering to the subject a DT-IL3 and one or more Jak inhibitors.

In some embodiments, a method of treatment comprises administering to the subject a DT-IL3 and one or more hypomethylating agents.

In some embodiments, a method of treatment comprises administering to the subject a DT-IL3, one or more Jak inhibitors, and one or more hypomethylating agents. In some embodiments, at least one Jak inhibitor and at least one hypomethylating agent is administered. In some embodiments, the at least one Jak inhibitor comprises ruxolitinib and the at least one hypomethylating agent comprises decitabine, azacitidine, and/or SGI-110.

In some embodiments, a method of treatment comprises administering to the subject a DT-IL3 and decitabine.

In some embodiments, a method of treatment comprises administering to the subject a DT-IL3 and azacitidine.

In some embodiments, a method of treatment comprises administering to the subject a DT-IL3 and SGI-110.

As used herein, the terms "subject" and "patient" are used interchangeably. As used herein, the term "subject" refers to an animal. In some embodiments, the animal is a mammal such as a non-primate (e.g., cows, pigs, horses, cats, dogs, rats, etc.) or a primate (e.g., monkey and human). In some embodiments, the subject is a human. In some embodiments, the subject is a nonhuman animal such as a farm animal (e.g., a horse, pig, or cow) or a pet (e.g., a dog or cat). In some embodiments, the subject is an elderly human. In some embodiments, the subject is a human adult. In some embodiments, the subject is a human child. In some embodiments, the subject is a pediatric human (i.e. human of less than 18 years of age). In some embodiments, the subject is a human infant.

In some embodiments, the subject has unfavorable cytogenetics. Subjects are determined to have a favorable or unfavorable cytogenetics on the basis of survival outcomes. Unfavorable cytogenetics refers to a cytogenetic risk profile associated with an unfavorable outcome. Unfavorable cytogenetics in a subject with MF may include, for example, complex karyotype (≥3 rearrangement abnormalities) or one or two abnormalities that include trisomy 8, deletion 7/7q, inversion 17q, inversion 3, deletion 5/5q, deletion 12p, or 11q23 rearrangement, and favorable cytogenetics include all other scenarios, including normal karyotype.

In some embodiments, the subject was refractory to prior treatment with one or more Jak inhibitors and/or one or more hypomethylating agents. As used herein, a subject is "refractory" to prior treatment if the patient has failed to achieve a response to a therapy such that the therapy is determined to not be therapeutically effective, such as: failure to reach clinical endpoint, including any of response, extended duration of response, extended disease free, survival, relapse free survival, progression free survival, and overall survival. In some embodiments, the subject was refractory to prior treatment with ruxolitinib. In some embodiments, the subject refractory to prior treatment with ruxolitinib has myelofibrosis (MF).

In some embodiments, the subject could not tolerate the full dose of a prior treatment with one or more Jak inhibitors and/or one or more hypomethylating agents. "Full dose," as used herein, refers to the dose(s) indicated in the prescribing information and/or a dose commonly used in clinical practice. In some embodiments, the maximum tolerated dose for a given patient was below the full dose. In other words, the subject could not tolerate the full dose of a prior treatment because of side effects. In some embodiments, the subject could not tolerate the full dose of a prior treatment with ruxolitinib. In some embodiments, the subject who could not tolerate the full dose of a prior treatment with ruxolitinib has MF.

In some embodiments, the subject has low platelet counts or was not eligible for treatment with ruxolitinib. In some embodiments, the subject with low platelet counts or who was not eligible for treatment with ruxolitinib has MF. In some embodiments, low platelet counts are measured as a platelet count at or below $5\times10^9$/L, at or below $10\times10^9$/L, at or below $20\times10^9$/L, at or below $30\times10^9$/L, at or below $40\times10^9$/L, or at or below $50\times10^9$/L. In some embodiments, patients may be ineligible for treatment with ruxolitinib due to renal impairment or hepatic impairment.

In some embodiments, the subject previously responded to a Jak inhibitor and/or a hypomethylating agent. In some embodiments, the subject who previously responded to a Jak inhibitor and/or a hypomethylating agent has MF. In some embodiments, the subject previously responded to ruxolitinib. A number of reasons for failure of prior therapy for MF have been characterized, such as myelosuppression, drug resistance, and persistence of the underlying malignant clone (See Pettit and Odenike *Curr Hematol Malig Rep.* 12(6):611-624 (2017)).

A. Myeloproliferative Neoplasm

In some embodiments, the MPN is polycythemia vera (PV), essential thrombocytosis (ET), myelofibrosis (MF), chronic myelomonocytic leukemia (CMML), chronic neutrophilic leukemia, chronic eosinophilic leukemia, systemic mastocytosis (SM), symptomatic hypereosinophilic disorder, or other bone marrow disorder that causes the production of excess red blood cells, white blood cells, and/or platelets. In some embodiments, the MPN is a primary eosinophilic disorder (PED).

In some embodiments, the MPN is myelofibrosis (MF). MF is characterized by replacement of the bone marrow with scar tissue. With bone marrow scarring, insufficient number of blood cells may be produced and lead to anemia, bleeding problems and infection risks. The liver and spleen may enlarge to attempt to produce additional blood cells.

In some embodiments, the MF is primary MF (PMF), post-polycythemia vera MF (post-PV MF), post-essential thrombocythemia MF (post-ET MF), primary MF in blast phase (PMF-BP), post-PV MF in blast phase, or post-ET MF in blast phase.

In some embodiments, the MPN is in blast phase.

In some embodiments, the MPN is PMF-BP, post-PV MF in blast phase, or post-ET MF in blast phase.

B. Treatment and Identification of Subjects with MPN

In some embodiments, a method for treating an MPN in a subject in need thereof, comprises identifying the MPN and administering an effective amount of a DT-IL3 and one or more Jak inhibitors and/or one or more hypomethylating agents to the subject in need thereof.

In some embodiments, the MPN is identified by physical examination, blood tests, bone marrow aspirate and biopsy, cytogenetic analysis, testing for mutations in the JAK2, MPL, ASXL1, TET2, or CALR gene, arterial oxygen saturation and carboxyhaemoglobin levels, neutrophil alkaline phosphatase levels, vitamin B12 or B12 binding capacity, or serum urate. In some embodiments, the mutation in the JAK2 gene is the JAK2V617F mutation.

In some embodiments, the patient has mutations in the JAK2, MPL, ASXL1, TET2, or CALR gene. In some embodiments, the patient has the JAK2V617F mutation.

C. Methods of Measuring Clinical Efficacy

In some embodiments, inhibiting an MPN results in a reduction in the proliferation of MPN cells, a stabilization in the amount of MPN cells, and/or a reduction in the amount of MPN cells. "MPN cells," as used herein refers to any abnormal cell of the bone marrow that gives rise to an MPN.

In some embodiments, inhibiting an MPN results in a reduction in spleen and/or liver size. In some embodiments, spleen size is measured by MRI or CT at different timepoints pre- and post-treatment. In some embodiments, the subject with MPN has an abnormally large spleen (i.e., splenomegaly) or abnormally large liver. In some embodiments, splenomegaly is defined as ≥5 cm below costal margin (BCM) by physical examination.

In some embodiments, the subject with MPN does not have an abnormally large spleen or abnormally large liver. In some embodiments, a subject with MPN is without baseline splenomegaly (5 cm BCM).

In some embodiments, the reduction in spleen size is a reduction of at least 25%, at least 29%, at least 33%, at least 35%, at least 40%, or at least 50% in spleen size. In some embodiments, the reduction in spleen size is a reduction of ≥33% in spleen size in subjects with baseline splenomegaly. Subjects who meet parameters for reduction in spleen measures are treatment "spleen responders."

In some embodiments, clinical efficacy is measured by improvements in splenomegaly. In some embodiments, improvements in splenomegaly in a group of subjects is measured by the percentage of spleen responders.

In some embodiments, improvements in splenomegaly is measured by the percent change in splenomegaly as measured by the cm palpable below the left costal margin.

In some embodiments, the subject has MF. Response criteria for MF include, but are not limited to, the exemplary response criteria in Table 2 below from the International Working Group-MRT and ELN for MF.

TABLE 2

| Response categories | Required criteria (for all response categories, benefit must last for ≥12 wk to qualify as a response) |
|---|---|
| CR | Bone marrow: *ge-adjusted normocellularity; <5% blasts; ≤grade 1 MF‡ and Peripheral blood: Hemoglobin ≥100 g/L and <UNL; neutrophil count ≥1 × 10$^9$/L and <UNL; Platelet count ≥100 × 10$^9$/L and <UNL; <2% immature myeloid cells‡ and Clinical: Resolution of disease symptoms; spleen and liver not palpable; no evidence of EMH |
| PR | Peripheral blood: Hemoglobin ≥100 g/L and <UNL; neutrophil count ≥1 × 10$^9$/L and <UNL; platelet count ≥100 × 10$^9$/L and <UNL; <2% immature myeloid cells‡ and Clinical: Resolution of disease symptoms; spleen and liver not palpable; no evidence of EMH or Bone marrow: *Age-adjusted normocellularity; <5% blasts; ≤grade 1 MF‡, and peripheral blood: Hemoglobin ≥85 but <100 g/L and <UNL; neutrophil count ≥1 × 10$^9$/L and <UNL; platelet count ≥50, but <100 × 10$^9$/L and <UNL; <2% immature myeloid cells‡ and Clinical: Resolution of disease symptoms; spleen and liver not palpable; no evidence of EMH |
| Clinical improvement (CI) | The achievement of anemia, spleen or symptoms response without progressive disease or increase in severity of anemia, thrombocytopenia, or neutropenia§ |
| Anemia response | Transfusion-independent patients: a ≥20 g/L increase in hemoglobin level‖ Transfusion-dependent patients: becoming transfusion-independent¶ |
| Spleen response# | A baseline splenomegaly that is palpable at 5-10 cm, below the LCM, becomes not palpable** or A baseline splenomegaly that is palpable at >10 cm, below the LCM, decreases by ≥50%** A baseline splenomegaly that is palpable at <5 cm, below the LCM, is not eligible for spleen response A spleen response requires confirmation by MRI or computed tomography showing ≥35% spleen volume reduction |
| Symptoms response | A ≥50% reduction in the MPN-SAF TSS†† |
| Progressive disease‡‡ | Appearance of a new splenomegaly that is palpable at least 5 cm below the LCM or A ≥100% increase in palpable distance, below LCM, for baseline splenomegaly of 5-10 cm or A 50% increase in palpable distance, below LCM, for baseline splenomegaly of >10 cm or Leukemic transformation confirmed by a bone marrow blast count of ≥20% or A peripheral blood blast content of ≥20% associated with an absolute blast count of ≥1 × 10(9)/L that lasts for at least 2 weeks |
| Stable disease | Belonging to none of the above listed response categories No longer meeting criteria for at least CI after achieving CR, PR, or CI, or Loss of anemia response persisting for at least 1 month or |

TABLE 2-continued

| Response categories | Required criteria (for all response categories, benefit must last for ≥12 wk to qualify as a response) |
|---|---|
| Relapse | Loss of spleen response persisting for at least 1 month |
| Cytogenetic remission | Recommendations for assessing treatment-induced cytogenetic and molecular changes At least 10 metaphases must be analyzed for cytogenetic response evaluation and requires confirmation by repeat testing within 6 months window CR: eradication of a preexisting abnormality PR: ≥50% reduction in abnormal metaphases (partial response applies only to patients with at least ten abnormal metaphases at baseline) |
| Molecular remission | Molecular response evaluation must be analyzed in peripheral blood granulocytes and requires confirmation by repeat testing within 6 months window CR: Eradication of a pre-existing abnormality PR: ≥50% decrease in allele burden (partial response applies only to patients with at least 20% mutant allele burden at baseline) |
| Cytogenetic/ molecular relapse | Re-emergence of a pre-existing cytogenetic or molecular abnormality that is confirmed by repeat testing |

Adapted from Tefferi et al., Blood 122(6):1395-98 (2013). In Table 2, CR=complete response or remission, PR=partial response or remission, EME=extramedullary hematopoiesis, LCM=left coastal margin, and UNL=upper limit of normal. * Baseline and posttreatment bone marrow slides are to be interpreted at one sitting by a central review process. Cytogenetic and molecular responses are not required for CR assignment. † Grading of MF is according to the European classification (Thiele et al., Haematologica 90:1128 (2005)). ‡ Immature myeloid cells constitute blasts+promyelocytes+myelocytes+metamyelocytes+nucleated red blood cells. In splenectomized patients, <5% immature myeloid cells is allowed. § See above for definitions of anemia response, spleen response, and progressive disease. Increase in severity of anemia constitutes the occurrence of new transfusion dependency or a ≥20 g/L decrease in hemoglobin level from pretreatment baseline that lasts for at least 12 weeks. Increase in severity of thrombocytopenia or neutropenia is defined as a 2-grade decline, from pretreatment baseline, in platelet count or absolute neutrophil count, according to the Common Terminology Criteria for Adverse Events (CTCAE) version 4.0. In addition, assignment to CI requires a minimum platelet count of ≥25 000×10(9)/L and absolute neutrophil count of ≥0.5×10(9)/L.‖ Applicable only to patients with baseline hemoglobin of <100 g/L. In patients not meeting the strict criteria for transfusion dependency at the time of study enrollment, but have received transfusions within the previous month, the pretransfusion hemoglobin level should be used as the baseline. ¶ Transfusion dependency before study enrollment is defined as transfusions of at least 6 units of packed red blood cells (PRBC), in the 12 weeks prior to study enrollment, for a hemoglobin level of <85 g/L, in the absence of bleeding or treatment-induced anemia. In addition, the most recent transfusion episode must have occurred in the 28 days prior to study enrollment. Response in transfusion-dependent patients requires absence of any PRBC transfusions during any consecutive "rolling" 12-week interval during the treatment phase, capped by a hemoglobin level of ≥85 g/L. # In splenectomized patients, palpable hepatomegaly is substituted with the same measurement strategy. ** Spleen or liver responses must be confirmed by imaging studies where a ≥35% reduction in spleen volume, as assessed by MRI or CT, is required. Furthermore, a ≥35% volume reduction in the spleen or liver, by MRI or CT, constitutes a response regardless of what is reported with physical examination. †† Symptoms are evaluated by the MPN-SAF TSS.17 The MPN-SAF TSS is assessed by the patients themselves and this includes fatigue, concentration, early satiety, inactivity, night sweats, itching, bone pain, abdominal discomfort, weight loss, and fevers. Scoring is from 0 (absent/as good as it can be) to 10 (worst imaginable/as bad as it can be) for each item. The MPN-SAF TSS is the summation of all the individual scores (0-100 scale). Symptoms response requires ≥50% reduction in the MPN-SAF TSS. ‡‡ Progressive disease assignment for splenomegaly requires confirmation my MRI or computed tomography showing a ≥25% increase in spleen volume from baseline. Baseline values for both physical examination and imaging studies refer to pretreatment baseline and not to posttreatment measurements.

III. Administration of Agents

These methods comprise a variety of administration schedules of DT-IL3 and the one or more Jak inhibitors and/or hypomethylating agents.

In some embodiments, the DT-IL3 is administered at least once a week. In some embodiments, the DT-IL3 is administered at least two times a week. In some embodiments, the DT-IL3 is administered at least three times a week.

In some embodiments, the one or more Jak inhibitors are administered at least once a week. In some embodiments, the one or more Jak inhibitors are administered at least two times a week. In some embodiments, the one or more Jak inhibitors are administered at least three times a week. In some embodiments, the one or more Jak inhibitors are administered every other day. In some embodiments, the one or more Jak inhibitors are administered every day. In some embodiments, the one or more Jak inhibitors are administered more than one time a day. In some embodiments, the one or more Jak inhibitors are administered twice-daily.

In some embodiments, the one or more hypomethylating agents are administered at least once a week. In some embodiments, the one or more hypomethylating agents are administered at least two times a week. In some embodiments, the one or more hypomethylating agents are administered at least three times a week. In some embodiments, the one or more hypomethylating agents are administered every day. In some embodiments, the one or more hypomethylating agents are administered twice a day. In some embodiments, the one or more hypomethylating agents are administered three times per day. In some embodiments, the one or more hypomethylating agents are administered daily for a period of time followed by a period when they are not administered. In some embodiments, the one or more hypomethylating agents are administered daily for a period of up to 7 days.

In some embodiments, the DT-IL3 and the (a) one or more Jak inhibitors and/or (b) one or more hypomethylating agents are administered over a period of one week or more. In some embodiments, the DT-IL3 and the (a) one or more Jak inhibitors and/or (b) one or more hypomethylating agents are administered over a period of two weeks or more. In some embodiments, the DT-IL3 and the (a) one or more Jak inhibitors and/or (b) one or more hypomethylating agents are administered for at least 3 consecutive days.

A. Treatment Cycles

In some embodiments, the DT-IL3 and the (a) one or more Jak inhibitors and/or (b) one or more hypomethylating agents are administered in multiple treatment cycles.

As used herein, "treatment cycle" refers to a period of administration of the DT-IL3 and the (a) one or more Jak inhibitors and/or (b) one or more hypomethylating agents. In some embodiments, there is a single treatment cycle. In some embodiments, there are multiple treatment cycles.

In some embodiments, there is a period of time between multiple treatment cycles when the DT-IL3 and the (a) one or more Jak inhibitors and/or (b) one or more hypomethylating agents are not administered. In some embodiments, the treatment cycles are at least 1 week apart, at least 2 weeks apart, at least 3 weeks apart, at least 4 weeks apart, at least 5 weeks apart, or a combination thereof.

In some embodiments, the DT-IL3 is administered for at least 3 consecutive days every 21 days for four cycles, followed by every 28 days for 3 cycles, and then every 42 days. In some embodiments, the one or more Jak inhibitors and/or the one or more hypomethylating agents are administered concurrently with the DT-IL3.

In some embodiments, the one or more Jak inhibitors and/or the one or more hypomethylating agents are administered at least once daily or at least twice daily.

In some embodiments, the one or more Jak inhibitors and/or the one or more hypomethylating agents are administered for at least the first 3 days, at least the first 4 days, at least the first 5 days, at least 6 days, or at least 7 days of at least one cycle.

In some embodiments, the one or more Jak inhibitors and/or the one or more hypomethylating agents are administered for at least the first 3 days, at least the first 4 days, at least the first 5 days, at least the first 6 days, or at least the first 7 days of a 28-day cycle for 3 cycles. In some embodiments, DT-IL3 is administered concurrently with the one or more Jak inhibitors and/or the one or more hypomethylating agents. In some embodiments, the one or more Jak inhibitors and/or the one or more hypomethylating agents are administered following administration of DT-IL3 for four 21-day cycles.

In some embodiments, the DT-IL3 and the (a) one or more Jak inhibitors and/or (b) one or more hypomethylating agents are administered until disease progression and/or unacceptable toxicity is obtained as determined, for example, by a treating physician.

IV. Pharmaceutical Compositions

In some embodiments, a pharmaceutical composition for treating or inhibiting a myeloproliferative neoplasm (MPN) in a subject in need thereof comprises an effective amount of a DT-IL3 and one or more Jak inhibitors and/or one or more hypomethylating agents. In some embodiments, the pharmaceutical composition further comprises a pharmaceutically acceptable excipient.

In some embodiments, the invention provides a pharmaceutical composition comprising an effective amount of a conjugate of the invention and a pharmaceutically acceptable carrier or vehicle. In some embodiments, a pharmaceutical composition comprises an effective amount of a conjugate of the invention and a pharmaceutically acceptable carrier or vehicle. The pharmaceutical compositions are suitable for veterinary and/or human administration.

The pharmaceutical compositions of the present invention can be in any form that allows for the composition to be administered to a subject.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of cancer the subject has, the use of the composition as part of a multi-drug regimen, the particular form of the composition of the invention, and the manner of administration.

The term "carrier" refers to a diluent, adjuvant or excipient, with which a composition of the invention is administered. Any auxiliary, stabilizing, thickening, lubricating and coloring agents can be used. In one embodiment, when administered to a subject, the compositions of the invention and pharmaceutically acceptable carriers are sterile. Water may be a carrier when the composition of the invention is administered intravenously. Saline solutions and aqueous dextrose and glycerol solutions can also be employed as liquid carriers, particularly for injectable solutions. The present compositions, if desired, can also contain minor amounts of pH buffering agents.

The liquid compositions of the invention, whether they are solutions, suspensions, or other like form, can also include one or more of the following: sterile diluents such as water for injection, saline solution, physiological saline, Ringer's solution, isotonic sodium chloride, fixed oils such as synthetic mono or diglycerides which can serve as the solvent or suspending medium, polyethylene glycols, glycerin, cyclodextrin, propylene glycol, or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, or phosphates; and agents for the adjustment of tonicity such as sodium chloride or dextrose. A parenteral composition can be enclosed in an ampoule, a disposable syringe, or a multiple-dose vial made of glass, plastic or other material. In some embodiments, physiological saline is an adjuvant. An injectable composition may be sterile.

The pharmaceutical compositions comprise an effective amount of a composition of the invention such that a suitable dosage will be obtained. Typically, this amount is at least 0.01% of the composition of the invention by weight of the pharmaceutical composition. When intended for oral administration, this amount can be varied to be between 0.1% and 80% by weight of the pharmaceutical composition. Oral pharmaceutical compositions may comprise from between 4% and 50% of the composition of the invention by weight of the pharmaceutical composition Pharmaceutical compositions may be prepared so that a parenteral dosage unit contains from between 0.01% and 2% by weight of the composition of the invention.

The pharmaceutical compositions can be administered by any convenient route, for example, by infusion or bolus injection, by absorption through epithelial or mucocutaneous linings (e.g., oral mucosa, rectal, and intestinal mucosa, etc.). Administration can be systemic or local. Various delivery systems are known, e.g., microparticles, microcapsules, capsules, etc., and may be useful for administering a composition of the invention. Methods of administration may include, but are not limited to, oral administration and parenteral administration; parenteral administration including, but not limited to, intradermal, intramuscular, intraperitoneal, intravenous, subcutaneous; intranasal, epidural, sublingual, intranasal, intracerebral, intraventricular, intrathecal, intravaginal, transdermal, rectally, by inhalation, or topically to the ears, nose, eyes, or skin. The mode of administration is left to the discretion of the practitioner, and will depend, in-part, upon the site of the medical condition (such as the site of cancer, a cancerous tumor, or a precancerous condition).

In some embodiments, the compositions of the invention are administered parenterally. In some embodiments, the compositions of the invention are administered intravenously. In another embodiment, the compositions of the invention are administered by continuous infusion. In a particular embodiment, the compositions of the invention are administered by an infusion that lasts for 15 minutes, 20 minutes, 30 minutes, 45 minutes, 1 hour, or 2 hours.

In some embodiments, it can be desirable to administer one or more compositions of the invention locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers. In certain embodiments, one or more compositions of the invention can be injected intraperitoneally.

In yet another embodiment, the compositions of the invention can be delivered in a controlled release system.

In some embodiments, a pump can be used to deliver the compositions of the invention (see, e.g., Sefton, *CRC Crit. Ref Biomed. Eng.* 1987, 14, 201; Buchwald et al., *Surgery* 1980, 88: 507; Saudek et al., *N. Engl. J. Med.* 1989, 321: 574). In some embodiments, the pump may be, but is not limited to, an insulin-like pump.

The present compositions can take the form of solutions, suspensions, tablets, pills, pellets, capsules, capsules containing liquids, powders, sustained-release formulations, suppositories, emulsions, aerosols, sprays, suspensions, or any other form suitable for use. Examples of suitable pharmaceutical carriers are described in *Remington's Pharmaceutical Sciences* by E. W. Martin.

In some embodiments, the compositions of the invention are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where a composition of the invention is to be administered by infusion, it can be dispensed, for example, with an infusion bottle containing sterile pharmaceutical grade water or saline. Where the composition of the invention is administered by injection, an ampoule of sterile water for injection or saline can be provided so that the ingredients can be mixed prior to administration.

The compositions of the present invention can comprise an additional active agent selected from among those including, but not limited to, an additional prophylactic agent, an additional therapeutic agent, an antiemetic agent, a hematopoietic colony stimulating factor, an adjuvant therapy, a vaccine or other immune stimulating agent, an antibody/antibody fragment-based agent, an anti-depressant and an analgesic agent. In some embodiments, the pharmaceutical composition comprises a pharmaceutically acceptable carrier or vehicle.

The pharmaceutical compositions can be prepared using methodology well known in the pharmaceutical art. For example, a composition intended to be administered by injection can be prepared by combining a composition of the invention with water so as to form a solution. A surfactant can be added to facilitate the formation of a homogeneous solution or suspension. Surfactants are complexes that can non-covalently interact with a composition of the invention so as to facilitate dissolution or homogeneous suspension of the composition of the invention in the aqueous delivery system.

EXAMPLES

Example 1. In Vitro Testing of a DT-IL3 and a Hypomethylating Agent

Figure 2A:
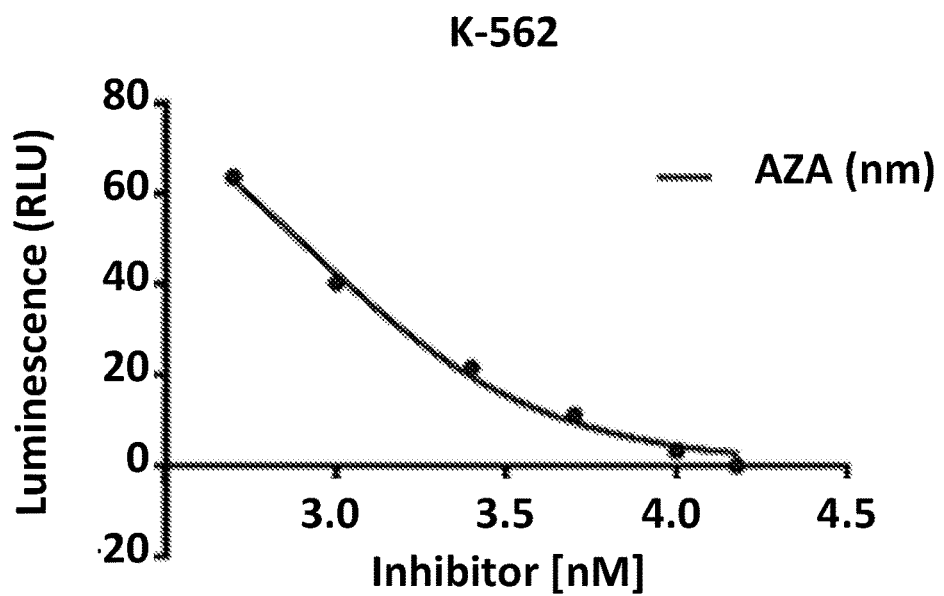
FIGS. 2A-2C show the results of cell viability assays with the CD123-expressing K562 cell line after treatment with increasing concentrations of azacitidine (AZA, FIG. 2A), DT-IL-3 (SL-401, FIG. 2B), or the combination of AZA and DT-IL3 (FIG. 2C) in vitro. AZA and DT-IL3 significantly reduced K562 cell viability when compared to AZA alone.
Figure 2B:
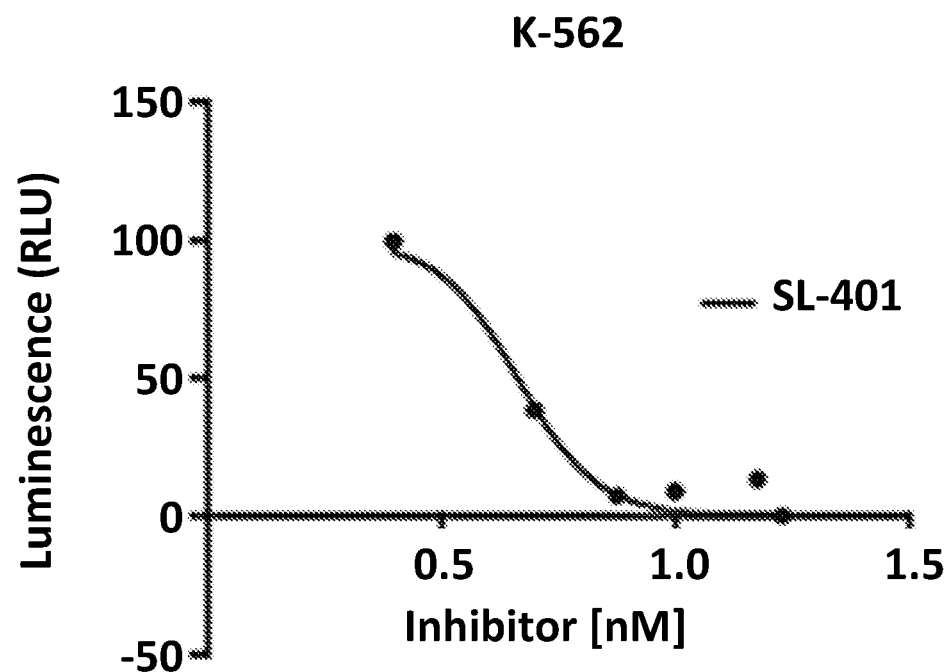
Figure 2C:
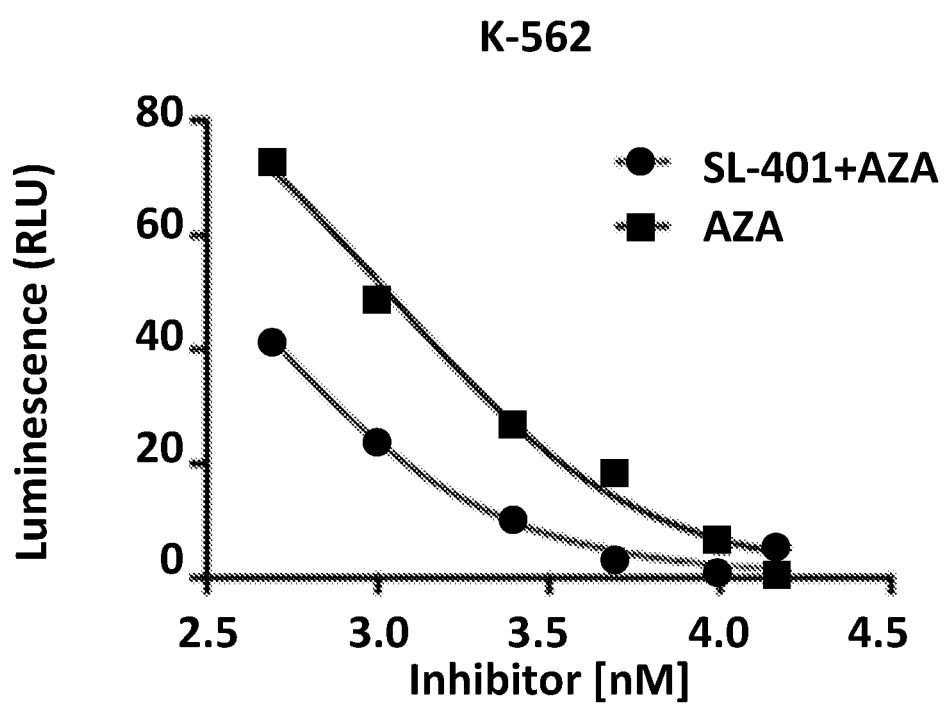

Preclinical studies were performed using human leukemia cell lines as well as primary mononuclear cells from the peripheral blood of CMML patients. In order to determine active concentrations of both the hypomethylating agent (HMA) azacitidine (AZA) and DT-IL3 (SL-401) in vitro, cells were exposed to increasing concentrations of AZA, DT-IL3, or the combination, and cell viability assays were performed. In the CD123-expressing K562 cell line, the IC50 of AZA and DT-IL3 was 772 μM and 4.8 nM, respectively (FIGS. 2A-2C). FIGS. 2A-2C show that AZA and DT-IL3 significantly reduced K562 cell viability when compared to AZA alone.

Figure 3A:
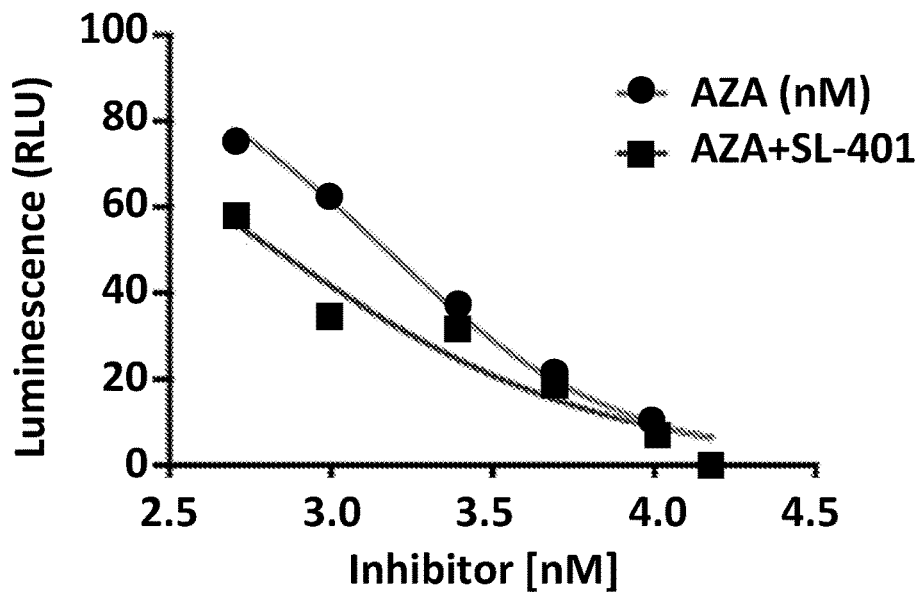
FIGS. 3A-3B show the results of cell viability assays with fresh mononuclear cells from the peripheral blood of CMML patients after treatment with AZA, DT-IL3, or the combination of AZA and DT-IL3 (SL-401) in vitro.
Figure 3B:
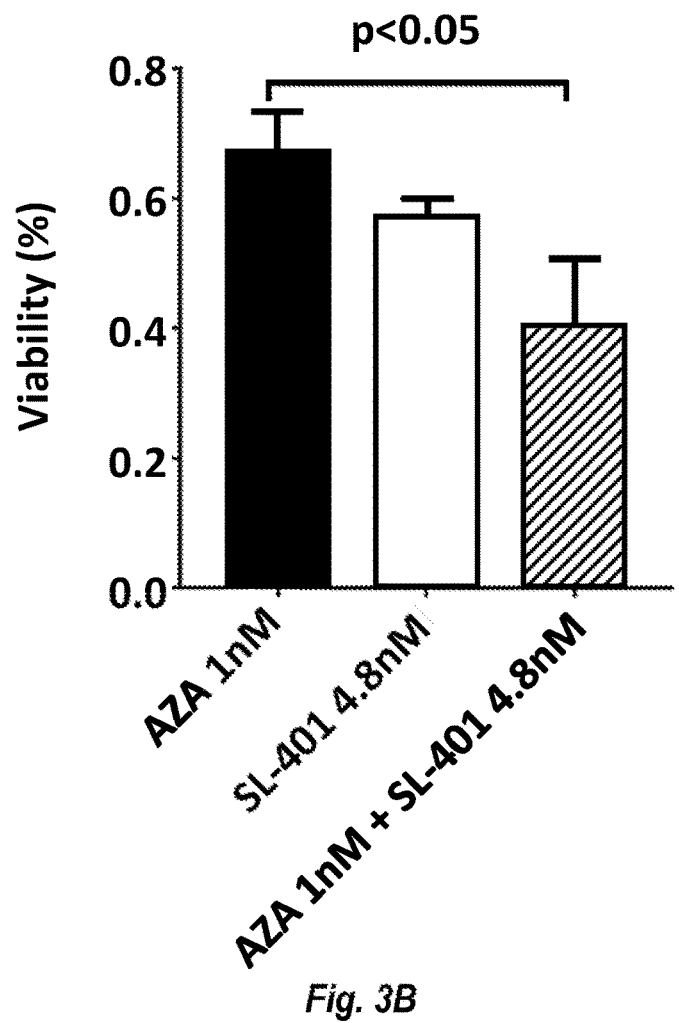

Cell viability assays were next performed using fresh mononuclear cells from the peripheral blood of CMML patients exposed to increasing concentrations of AZA and DT-IL3 in vitro. The IC50 of single agent AZA was 1442 μM, whereas the IC50 of the combination of AZA and DT-IL3 (at a concentration of 4.8 nM) was 725 μM (FIG. 3A). The addition of 4.8 nM DT-IL3 to 1 μM AZA in this assay caused a significant reduction in cell viability compared to 1 μM AZA alone (FIG. 3B; p<0.05).

Figures 4A, 4B:
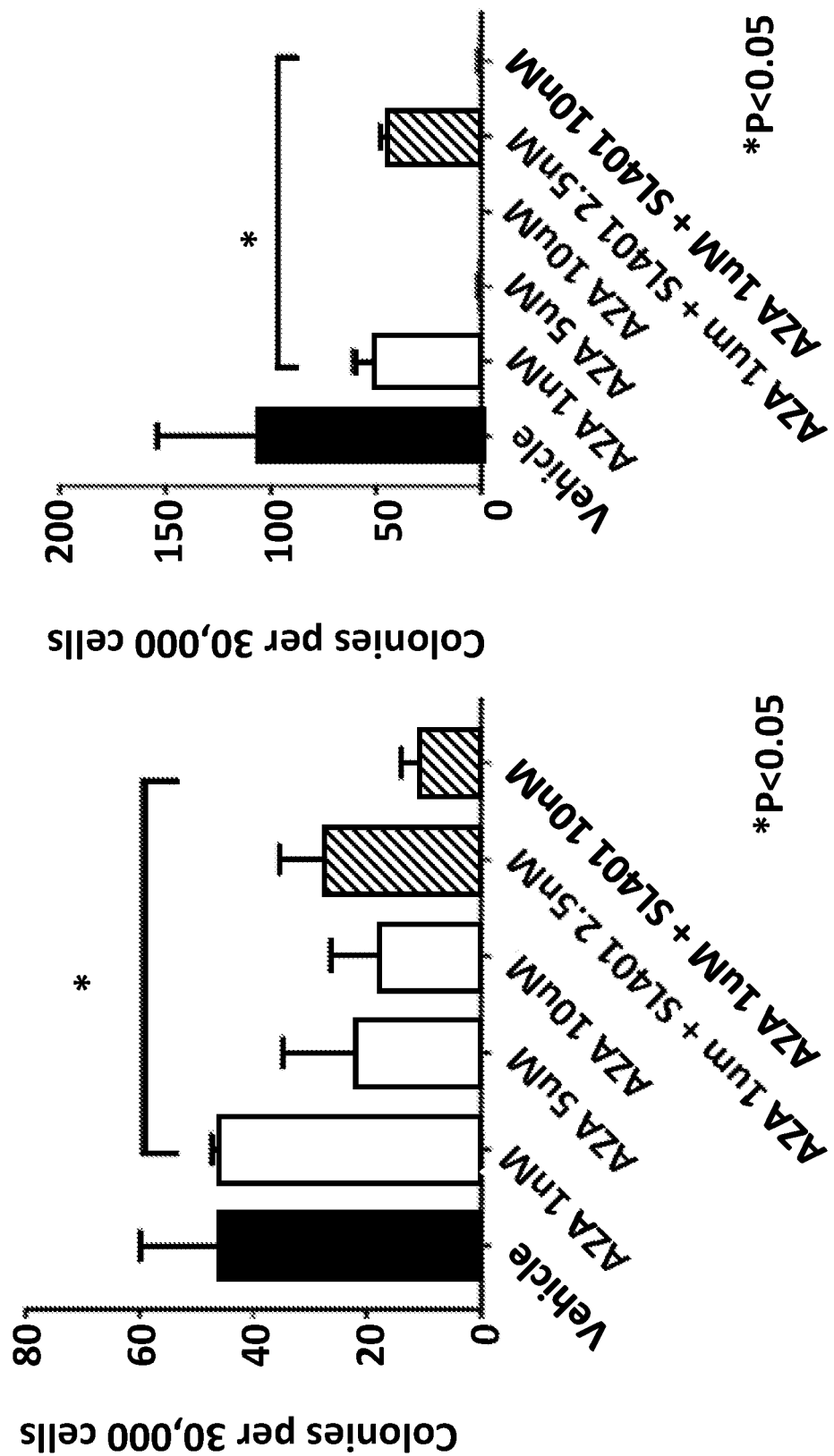
FIGS. 4A-4D show the results of colony forming assays using fresh mononuclear cells from the peripheral blood of CMML patients.
Figure 4C:
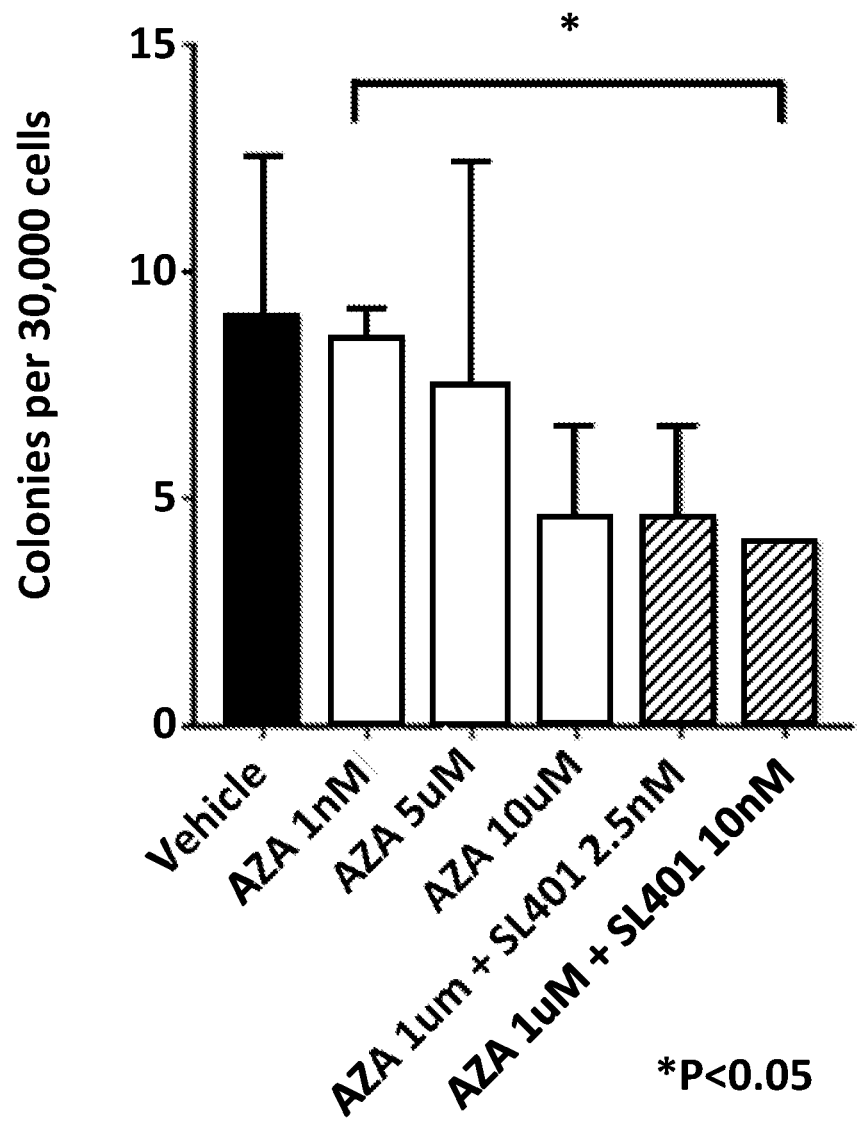
Figure 4D:
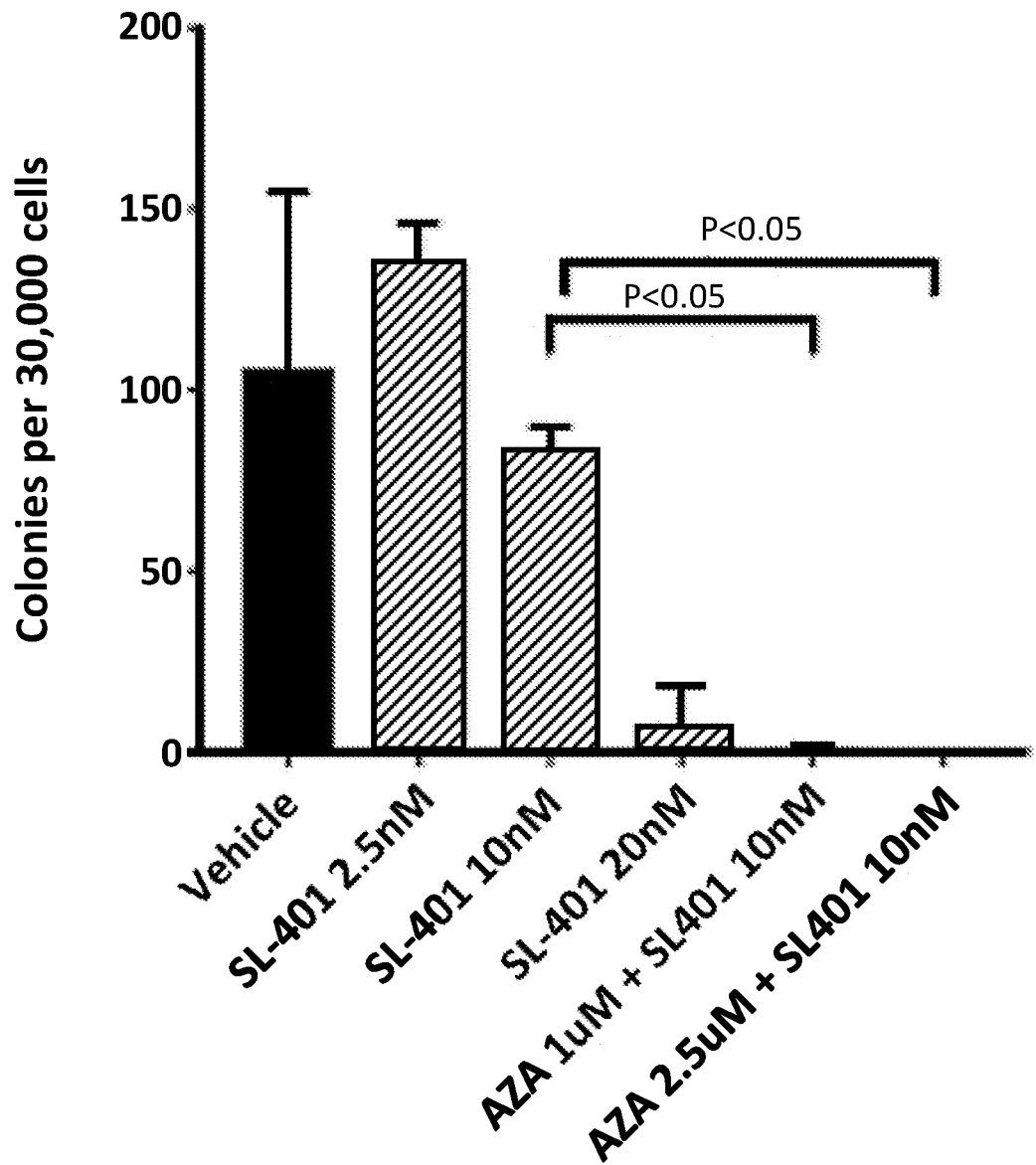

In colony forming assays using fresh mononuclear cells from the peripheral blood of CMML patients, the combination of AZA and DT-IL3 significantly reduced colony formation when compared to single agent AZA (FIGS. 4A-4C, p<0.05) Similarly, addition of AZA to increasing concentrations of DT-IL3 significantly reduced colony formation compared to single agent DT-IL3 (FIG. 4D, p<0.05). Importantly, a combination effect was observed across patient samples with high risk genotypes, including those with mutations in NRAS/ASXL1/TET2 (FIG. 4C) and mutations in SRSF2/TET2/STAG2 (FIG. 4A).

Current therapeutic options for CMML are limited and the treatment of CMML remains a significant unmet medical need. Although HMA therapy has demonstrated efficacy in CMML, the effects are often limited in extent and duration. The preclinical data, including in primary CMML samples, demonstrates a potential therapeutic role for the combination of an HMA and DT-IL3 in CMML. See FIGS. 2A-2C, 3A-3B, and 4A-4D.

Example 2. Clinical Trials of Treatment-Naïve Patients

Clinical trials can assess the efficacy of a DT-IL3 and one or more Jak inhibitors and/or one or more hypomethylating agents in treatment-naïve patients with MPN. By treatment-naïve, it is meant that these patients have not previously received treatment for MPN. For example, these patients will not have received previous treatment with a Jak inhibitor or a hypomethylating agent.

The patients in the trial may have a range of different types of MPN. Alternatively, all patients in the trial may have myelofibrosis.

Patients may be diagnosed with MPN based on physical examination, blood tests, bone marrow aspirate and biopsy, cytogenetic analysis, testing for mutations in the JAK2, MPL, ASXL1, TET2, or CALR gene, arterial oxygen saturation and carboxyhaemoglobin levels, neutrophil alkaline phosphatase levels, vitamin B12 or B12 binding capacity, or serum urate levels.

In some embodiments, the patient has mutations in the JAK2, MPL, ASXL1, TET2, or CALR gene. In some embodiments, the patient has the JAK2V617F mutation.

The trial may have an adaptive design. In other words, the trial may allow modifications to the trial and/or procedures during the trial. Alternatively, the trial may have set treatments groups that are maintained throughout the trial.

Treatment groups may include comparison of DT-IL3 to the combination of DT-IL3 and one or more Jak inhibitors and/or one or more hypomethylating agents.

Treatment groups may include of comparison one or more Jak inhibitors to the combination of DT-IL3 and one or more Jak inhibitors and/or one or more hypomethylating agents.

Treatment groups may include of comparison one or more hypomethylating agents to the combination of DT-IL3 and one or more Jak inhibitors and/or one or more hypomethylating agents.

With an adaptive design, patients who fail treatment with one or more hypomethylating agents or one or more Jak inhibitors may be begin treatment with the combination of DT-IL3 and one or more Jak inhibitors and/or one or more hypomethylating agents.

Treatment success or failure may be assessed by standard measures used in MPN trials, such as reduction in spleen and/or liver size. Changes in blood composition, disease recurrence, and patient survival would also be assessed over treatment. Toxicities and adverse events would be measured during treatment.

Any of the doses of agents and treatment cycles described in this application may be used. The DT-IL3 may be $DT_{388}IL-3$. The Jak inhibitor may be ruxolitinib. The one or more hypomethylating agent may be azacitidine, decitabine, and/or SGI-110.

Applicant expects that the treated patients will see clinical improvement.

Example 3. Clinical Trials of Refractory Patients

Clinical trials may assess the efficacy of DT-IL3 and one or more Jak inhibitors and/or one or more hypomethylating agents in patients with MPN who were refractory to prior treatment or who could not tolerate the full dose of a prior treatment. The prior treatment may be one or more hypomethylating agents or one or more Jak inhibitors. Ruxolitinib may be the prior treatment.

A clinical trial of refractory patients may not include a treatment arm of the prior treatment to which the patient was refractory. A clinical trial of refractory patients may compare the efficacy of DT-IL3 and one or more Jak inhibitors and/or one or more hypomethylating agents to the efficacy of an agent with which the patient was not previously treated. For example, a trial of patients refractory to ruxolitinib may include a treatment group of a hypomethylating agent and a treatment group of DT-IL3 and one or more Jak inhibitors and/or one or more hypomethylating agents.

Besides selection of patients, a clinical trial in refractory patients may have similar or identical parameters to a clinical trial in treatment-naïve patients.

Applicant expects that the treated patients will see clinical improvement.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, all numeric values are presumed to "about." As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A method for treating or inhibiting a myeloproliferative neoplasm (MPN) in a human subject in need thereof, comprising administering to the subject a diphtheria toxin-human interleukin-3 conjugate (DT-IL3) and
  a. one or more Jak inhibitors and/or
  b. one or more hypomethylating agents.

2. The method of claim 1, wherein the DT-IL3 is administered at a dose:
  a. of 1 µg/kg or greater;
  b. of 2 µg/kg to 20 µg/kg, 9 µg/kg to 12 µg/kg, or 4 µg/kg to 12 µg/kg;
  c. of 5 µg/kg, 7 µg/kg, 9 µg/kg, or 12 µg/kg; or
  d. that is the maximum tolerated dose.

3. The method of claim 1, wherein the DT-IL3 and the one or more Jak inhibitors and/or hypomethylating agents are administered:
  a. at least once a week, at least two times a week, or at least three times a week;
  b. over a period of one week or more, or over a period of two weeks or more;
  c. for at least 3 consecutive days;
  d. in multiple treatment cycles; and/or
  e. until disease progression and/or unacceptable toxicity is obtained.

4. The method of claim 3, wherein:
  a. the treatment cycles are at least 1 week apart, at least 2 weeks apart, at least 3 weeks apart, at least 4 weeks apart, at least 5 weeks apart, or a combination thereof;
  b. the DT-IL3 is administered for at least 3 consecutive days every 21 days for four cycles, followed by every 28 days for 3 cycles, and then every 42 days; and/or
  c. wherein the one or more Jak inhibitors are administered at least once daily, or at least twice daily; and/or
  d. the one or more hypomethylating agents are administered for at least the first 3 days, at least the first 4 days, at least the first 5 days, at least the first 6 days, or at least the first 7 days of at least one cycle.

5. The method of claim 4, wherein the one or more hypomethylating agents are administered for at least the first 3 days of a 28-day cycle for 3 cycles following administration of DT-IL3 for four 21-day cycles.

6. The method of claim 1, wherein the human subject has unfavorable cytogenetics.

7. The method of claim 1, wherein the DT-IL3 is a chemical conjugate.

8. The method of claim 1, wherein the DT-IL3 is a recombinantly expressed protein.

9. The method of claim 8, wherein the DT-IL3 is expressed as a single polypeptide comprising the catalytic and translocation domains of diphtheria toxin and human IL-3.

10. The method of claim 9, wherein the DT-IL3 comprises amino acid residues 1 to 388 of diphtheria toxin linked via a peptide bond to human IL-3.

11. The method of claim 1, wherein the inhibition results in a reduction in the proliferation of MPN cells, a stabilization in the amount of MPN cells, a reduction in the amount of MPN cells, and/or a reduction in spleen and/or liver size.

12. The method of claim 1, wherein the MPN is polycythemia vera, essential thrombocytosis, myelofibrosis, chronic myelomonocytic leukemia, chronic neutrophilic leukemia, chronic eosinophilic leukemia, systemic mastocytosis, symptomatic hypereosinophilic disorder, or other bone marrow disorder that causes the production of excess red blood cells, white blood cells, and/or platelets.

13. The method of claim 1, wherein the one or more Jak inhibitors comprises ruxolitinib.

14. The method of claim 1, wherein the one or more hypomethylating agents comprise azacitidine, decitabine, and/or SGI-110.

15. The method of claim 1, wherein at least one Jak inhibitor and at least one hypomethylating agent is administered.

16. The method of claim 15, wherein the at least one Jak inhibitor comprises ruxolitinib and the at least one hypomethylating agent comprises decitabine, azacitidine, and/or SGI-110.

17. The method of claim 1, wherein the human subject:
  a. was refractory to prior treatment with one or more Jak inhibitors and/or one or more hypomethylating agents;
  b. could not tolerate the full dose of a prior treatment with one or more Jak inhibitors and/or one or more hypomethylating agents;
  c. has low platelets counts or was not eligible for treatment with one or more Jak inhibitors;
  d. previously responded to one or more Jak inhibitors and/or one or more hypomethylating agents;
  e. has mutations in the JAK2, MPL, ASXL1, TET2, or CALR gene; and/or
  f. has an MPN in blast phase.

18. The method of claim 17, wherein the one or more Jak-inhibitors comprises ruxolitinib.

19. The method of claim 17, wherein the human subject has the JAK2V617F mutation.

\* \* \* \* \*